(12) United States Patent
Giovannini et al.

(10) Patent No.: US 10,849,907 B2
(45) Date of Patent: Dec. 1, 2020

(54) IMIDAZOPYRIDINE DERIVATIVES AND THE USE THEREOF AS MEDICAMENT

(71) Applicant: Boehringer Ingelheim International GmbH, Ingelheim am Rhein (DE)

(72) Inventors: Riccardo Giovannini, Biberach an der Riss (DE); Angelo Ceci, Mittelbiberach (DE); Georg Dahmann, Biberach an der Riss (DE); Cornelia Dorner-Ciossek, Warthausen (DE); Lothar Kussmaul, Schemmerhofen (DE); Roland Pfau, Biberach an der Riss (DE); Dieter Wiedenmayer, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 5 days.

(21) Appl. No.: 16/211,355

(22) Filed: Dec. 6, 2018

(65) Prior Publication Data
US 2019/0175605 A1    Jun. 13, 2019

(30) Foreign Application Priority Data

Dec. 8, 2017 (EP) ................................ 17206152

(51) Int. Cl.
| | | |
|---|---|---|
| A61K 31/5377 | (2006.01) | |
| A61P 25/24 | (2006.01) | |
| A61P 25/00 | (2006.01) | |
| C07D 471/04 | (2006.01) | |

(52) U.S. Cl.
CPC .......... *A61K 31/5377* (2013.01); *A61P 25/00* (2018.01); *A61P 25/24* (2018.01); *C07D 471/04* (2013.01); *C07B 2200/07* (2013.01)

(58) Field of Classification Search
CPC ................................................ A61K 31/5377
See application file for complete search history.

(56) References Cited

U.S. PATENT DOCUMENTS

2002/0055519 A1   5/2002   Thompson et al.

FOREIGN PATENT DOCUMENTS

| WO | 2003010159 A1 | 2/2003 | |
| WO | 2010088408 A2 | 8/2010 | |
| WO | 2014060398 A1 | 4/2014 | |
| WO | 2015130905 A1 | 9/2015 | |
| WO | 2016029146 | 2/2016 | |
| WO | WO-2016029146 A1 * | 2/2016 | ........... C07D 471/04 |

OTHER PUBLICATIONS

International Search Report and Written Opinion for PCT 2018/083728 dated Feb. 4, 2019.

Murrough, "Antidepressant Efficacy of Ketamine in Treatment-Resistant Major Depression: A Two Site Randomized Controlled Trial", Am. J. Psychiatry, 2013, vol. 170, p. 1134-1142.
Singh, "Intravenous Eskatamine in Adult Treatment-Resistant Depression: A double-Blind, Double-Randomization, Placebo Controlled Study", Society of Biological Psychiatry, vol. 80, 2016, p. 424-431.
Berman, "Antidepressant effects of Ketamine in depressed patients", Biological Psychiatry, vol. 47, 2000, p. 351-354.
Serafini, "The Role of Ketamine in Treatment-Resistant Depression", Current Neuropharmacology, vol. 12, 2014, p. 444-461.
Krystal, "Subanesthetic Effects of the Noncompetitive NMDA Antagonist, Ketamine in Humans", Arch. Gen. Psychiatry, 1994, vol. 51, p. 199-214.
Paoletti, "NMDA Receptor subunit Diversity: impact on receptor properties, synaptic plasticity and disease", Nature Reviews, vol. 14, 2013.
Mony, "Allosteric Modulators of NR2B-containing NMDA receptors: molecular mechanisms and therapeutic potential", British Journal od Pharmacology, 2009.
Chaffey, NMDA receptors subtypes: Structure, function and therapeutics:, Current Anasthesia and Critical Care, vol. 19, 2008, p. 183-201.
Preskorn, "An innovative Design to Establish Proof of Concept of Antidepressant Effects of the NR2B Subunit Selective N-Methyl-D-Aspartate Antagonist, CP-101,606, in Patients with Treatment Refractory Major Depressive Disorder", J. of Clinical Psychopharmacology, 2008, vol. 28, p. 631-637.
Miller, "GluN2B-contaning NMDA receptors regulate depression-like behavior and are critical for the rapid antidepressant actions of ketamine", eLife3e03581, 2014.
Kiselycznyk, "NMDA receptor subunits and associated signaling molecules mediating anti-depressant related effects of NMDA-GluN2B antagonism", Bhav. Nrain Res. 2015, p. 89-95.
Jimemez-Sanchez, "The Role of GluN2A and GluN2B Subunits on the effects of NMDA receptor Antagonists in modeling Schizophrenia and treating Refractory Depression", Neuropsychopharmacology, 2014.
Taylor, "Absolute Oral Bioavailability of Traxoprodil in Cytochrome P450 2D6 Extensive and Poor Metabolisers", Clin. Pharmacokinet, 2006, vol. 45, p. 989-1001.

(Continued)

*Primary Examiner* — John S Kenyon
(74) *Attorney, Agent, or Firm* — Robert J. Kajubi

(57) ABSTRACT

The present invention relates to imidazopyridines of formula A

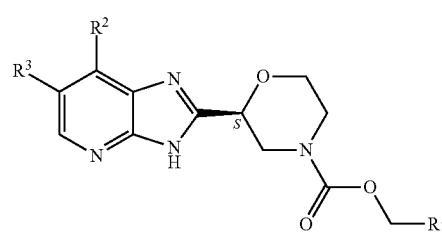

processes for their preparation, pharmaceutical compositions containing them and their use in therapy, particularly in the treatment or prevention of conditions having an association with NR2B negative allosteric modulating properties.

49 Claims, No Drawings

(56) References Cited

OTHER PUBLICATIONS

Addy, "Single dose Administration of MK-0657, an NR2B-Selective NMDA Antagonist", J. of Clinical Pharmacology, 2009, p. 856-864.

Layton, "Discovery of 3-Substituted Aminocyclopentanes as Potent and Orally Bioavailable NR2B Subtype-Selective NMDA Antagonists", ACS Chem. Neuroscience, 2011.

Traynelis, Glutamate Receptor Ion Channels: Structure, Regualtion and Function, Pharmacology reviews, 2010, vol. 62.

Beinat, Insights into Structure Related Activity Relationships and CNS Therapeutic Applications of NR2B Selective Antagonists, Current Medicinal Chem., 2010, vol. 17.

Chaffey, NMDA receptor subtypes, Current Anesthesia and Critical Care, 2008, vol. 19, p. 183-201.

Mony, Allosteric modulators of NR-2B-containing NMDA receptors, Bristish Journal of Pharmacology, vol. 157, 2009.

Preskorn, An Innovative Design to Establish Proof of Concept of the Antidepressant effects of the NR2B Subunit Selective N-Methyl D-Aspartate Antagonist CP-101, 606, Journal of Clinical Pharmacology, vol. 28, 2008.

Beinat, Insights into Structure related activity relationships, Current Medicinal Chem, 2010. vol. 17, p. 4166-4190.

Serafini, The Role of Ketamine in Treatment resistant Depression, Current Neurapharmacology, 2014, vol. 10, p. 444-461.

\* cited by examiner

IMIDAZOPYRIDINE DERIVATIVES AND THE USE THEREOF AS MEDICAMENT

FIELD OF THE INVENTION

The present invention relates to novel imidazopyridines processes for their preparation, pharmaceutical compositions containing them and their use in therapy, particularly in the treatment or prevention of conditions having an association with NR2B negative allosteric modulating properties.

BACKGROUND OF THE INVENTION

Extensive studies over the past twenty years have indicated that N-methyl-D-aspartate receptors (NMDA) play a relevant role in Alzheimer's disease, Parkinson's disease, dyskinesia, stroke, motor neuron disease, psychosis, epilepsy, anxiety, schizophrenia and pain.

The non-selective NMDA receptor antagonist ketamine, (racemic as well as the S enantiomer), a medication mainly used for starting and maintaining anaesthesia, has demonstrated over the last years clinical efficacy in treating major depressive disorder (MDD) at subanaesthetic doses (Murrough et al. 2013, Am J Psychiatry. 170: 1134; Singh et al. 2016, Biol Psychiatry. 80: 424). More precisely, ketamine elicits a rapid onset of efficacy which lasts several days in MDD patients insufficiently responding to standard drug therapy (Berman et al. 2000. Biol Psychiatry 47:351, Serafini et al. 2014. Curr. Neuropharmacol. 12:444). However, non-selective NMDA receptor antagonists have a range of undesirable effects which limit their application. In particular dissociative and psychogenic side effects are prominent for the non-selective NMDA receptor antagonists such as ketamine (Krystal et al. 1994. Arch. Gen. Psychiatry 51:199). In the early 1990s, it was found that multiple NMDA receptor subtypes exist, which contain different NR2(A-D) subunits (Paoletti et al., 2013 Nat Rev. Neurosci 14:383). More recently, NR2B subtype selective NMDA receptor negative allosteric modulators (NR2B NAM) have raised interest and have shown potential in a wide range of clinical indications, such as attention, emotion, mood, and pain, as well as being involved in a number of different human disorders (Mony et. al. 2009. Br. J. Pharmacol. 157:1301; Chaffey et al., Current Anaesthesia & Critical Care 19, 183). In particular, NR2B NAM have also demonstrated antidepressant efficacy in the early stage of clinical trials (Preskorn et al. 2008. J Clin Psychopharmacol 70:58). Preclinical studies using NR2B NAM as well as applying various transgenic mice strains have shown that NR2B containing NMDA-receptors are mediating the positive effect of ketamine in e.g. the Forced Swim Test (Miller et al. 2014 eLife 3:e03581; Kiselycznyk et al. 2015, Behav Brain Res, 287:89). Furthermore, selective NR2B NAM have advantages over unselective NMDA receptor antagonists, such as ketamine, due to greatly diminished dissociative and psychotomimetic side effects (Jimenez-Sanchez et al. 2014. Neuropsychopharmacology 39:2673). NR2B NAM described to date have exhibited drawbacks with regard to their receptor pharmacology and/or to other drug properties which have limited potential use in human drug therapy (Taylor, et al., 2006, Clin Pharmacokinet. 45: 989; Addy et al. 2009 J of Clinical Pharmacology 49:856)).

WO2016/29146 discloses compounds of formula (I)

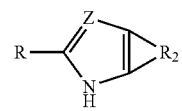

that are inhibitors of methionyl-tRNA synthetase (MetRS) being useful as antibiotics. Formula (I) in WO2016/29146 encompasses the specific examples 1734, 1744, 1745, 1757 1758, 1785 and 1790 which exhibit a benzimidazole or imidazopyridine substructure.

The compounds of the present invention have surprisingly been found to be potent NR2B negative allosteric modulators (see table 1), whereas the specific examples 1734, 1744, 1745, 1757, 1758, 1785 and 1790 of WO2016/29146 show rather poor negative allosteric modulation of the NR2B ion channel or no activity at all (see table 2).

Further, the compounds of the present invention show good membrane permeability and low to moderate in vitro efflux (see table 3 for MDCK assay MDR1 (p-GP), and table 4 for MDCK assay BCRP). Therefore, compounds of the present invention are expected to show a favorable brain penetration which is required for efficacious CNS medicaments.

The MDCK assays provide information on the potential of a compound to pass the blood brain barrier. Permeability measurements across polarized, confluent MDCK-MDR1 cell monolayers grown on permeable filter supports are used as an in vitro absorption model: apparent permeability coefficients (PE) of the compounds across the MDCK-MDR1 cell monolayers are measured (pH 7.4, 37° C.) in apical-to-basal (AB) and basal-to-apical (BA) transport direction. The AB permeability (PEAB) represents drug absorption from the blood into the brain and the BA permeability (PEBA) drug efflux from the brain back into the blood via both, passive permeability as well as active transport mechanisms mediated by efflux and uptake transporters that are expressed on the MDCK-MDR1 cells, predominantly by the overexpressed human MDR1. Identical or similar permeabilities in both transport directions indicate passive permeation, vectorial permeability points to additional active transport mechanisms. Higher PEBA than PEAB (PEBA/PEAB >5) indicates the involvement of active efflux mediated by MDR1, which might compromise the goal to achieve sufficient brain exposure. Therefore, this assay provides valuable support for selection of compounds applicable for further in vivo testing. High permeability not limited by efflux at the blood brain barrier is a favourable characteristic for compounds that are to be used for drugs acting primarily in the CNS. Similar concepts are applicable to the MDCK BCRP assay and its interpretation; consequently, to ensure high permeability at the blood brain barrier, it is highly preferred to minimize the efflux (efflux <5) at both MDR1 and BCRP transporters.

Further, the compounds of the present invention are metabolically stable in human liver microsomes (see table 5, metabolic stability). Therefore, compounds of the present invention are expected to have a favorable in vivo clearance and thus the desired duration of action in humans.

Stability in human liver microsomes refers to the susceptibility of compounds to biotransformation in the context of selecting and/or designing drugs with favorable pharmacokinetic properties. The primary site of metabolism for many drugs is the liver. Human liver microsomes contain the cytochrome P450s (CYPs), and thus represent a model system for studying drug metabolization in vitro. Enhanced stability in human liver microsomes is associated with several advantages, including increased bioavailability and adequate half-life, which can enable lower and less frequent dosing of patients. Thus, enhanced stability in human liver microsomes is a favorable characteristic for compounds that are to be used for drugs.

Consequently, compounds of the present invention must be more viable for human use.

SUMMARY OF THE INVENTION

The objective technical problem is thus to provide potent NR2B negative allosteric modulators.

The present invention provides novel imidazopyridines of formula A

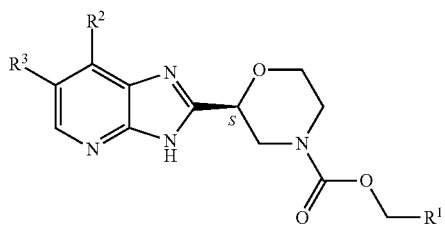

in which
R¹ represents phenyl which is optionally substituted with 1 to 3 substituents selected from the group consisting of fluoro, chloro, methyl, ethyl, cyclopropyl, F₂HC—, FH₂C—, F₃C—;
R² represents hydrogen, methyl;
R³ represents hydrogen, fluoro;
or a salt thereof, particularly a pharmaceutically acceptable salt thereof.

In another embodiment, in the general formula A, R¹ has the same meaning as defined in any of the preceding embodiments, and
R² represents hydrogen;
R³ represents fluoro.

In another embodiment, in the general formula A, R¹ has the same meaning as defined in any of the preceding embodiments, and
R² represents methyl;
R³ represents hydrogen.

In another embodiment, in the general formula A, R¹ has the same meaning as defined in any of the preceding embodiments, and
R² and R³ represent hydrogen.

In another embodiment, in the general formula A, R² and R³ have the same meaning as defined in any of the preceding embodiments, and
R¹ represents phenyl which is optionally substituted with 1 or 2 substituents selected from the group consisting of fluoro, chloro, methyl, F₂HC—.

In another embodiment, in the general formula A, R² and R³ have the same meaning as defined in any of the preceding embodiments, and
R¹ represents

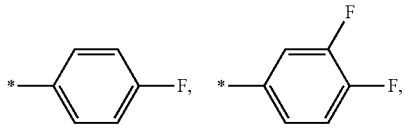

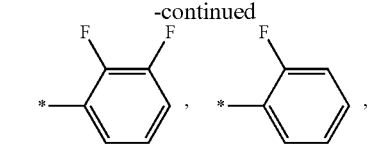

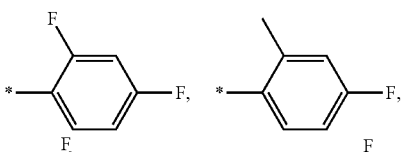

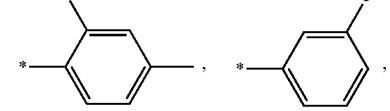

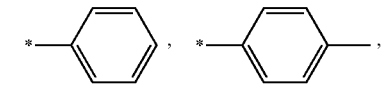

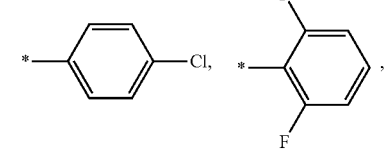

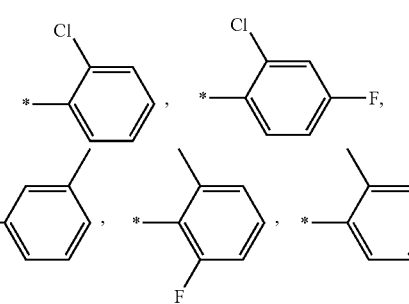

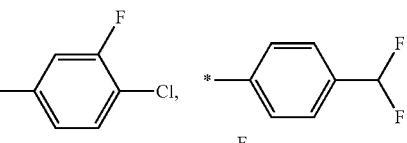

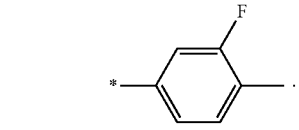

DETAILED DESCRIPTION OF THE INVENTION

The present invention provides novel imidazopyridines of general formula A that unexpectedly are potent NR2B negative allosteric modulators.

Another aspect of the invention refers to compounds according to formula A as NR2B negative allosteric modulators having appropriate membrane permeability and low to moderate in vitro efflux.

Another aspect of the invention refers to compounds according to formula A as NR2B negative allosteric modulators having high metabolic stability in human liver microsomes.

Another aspect of the invention refers to compounds according to formula A as NR2B negative allosteric modulators having appropriate membrane permeability, low to moderate in vitro efflux and high metabolic stability in human liver microsomes.

Another aspect of the invention refers to pharmaceutical compositions, containing at least one compound according to formula A optionally together with one or more inert carriers and/or diluents.

A further aspect of the present invention refers to compounds according to formula A, for the use in the prevention and/or treatment of disorders associated with NR2B negative allosteric modulators.

Another aspect of the invention refers to processes of manufacture of the compounds of the present invention.

Preparation

The following schemes shall illustrate generally how to manufacture the compounds according to general formula A and the corresponding intermediate compounds by way of example. The abbreviated substituents may be as defined above if not defined otherwise within the context of the schemes.

Scheme 1

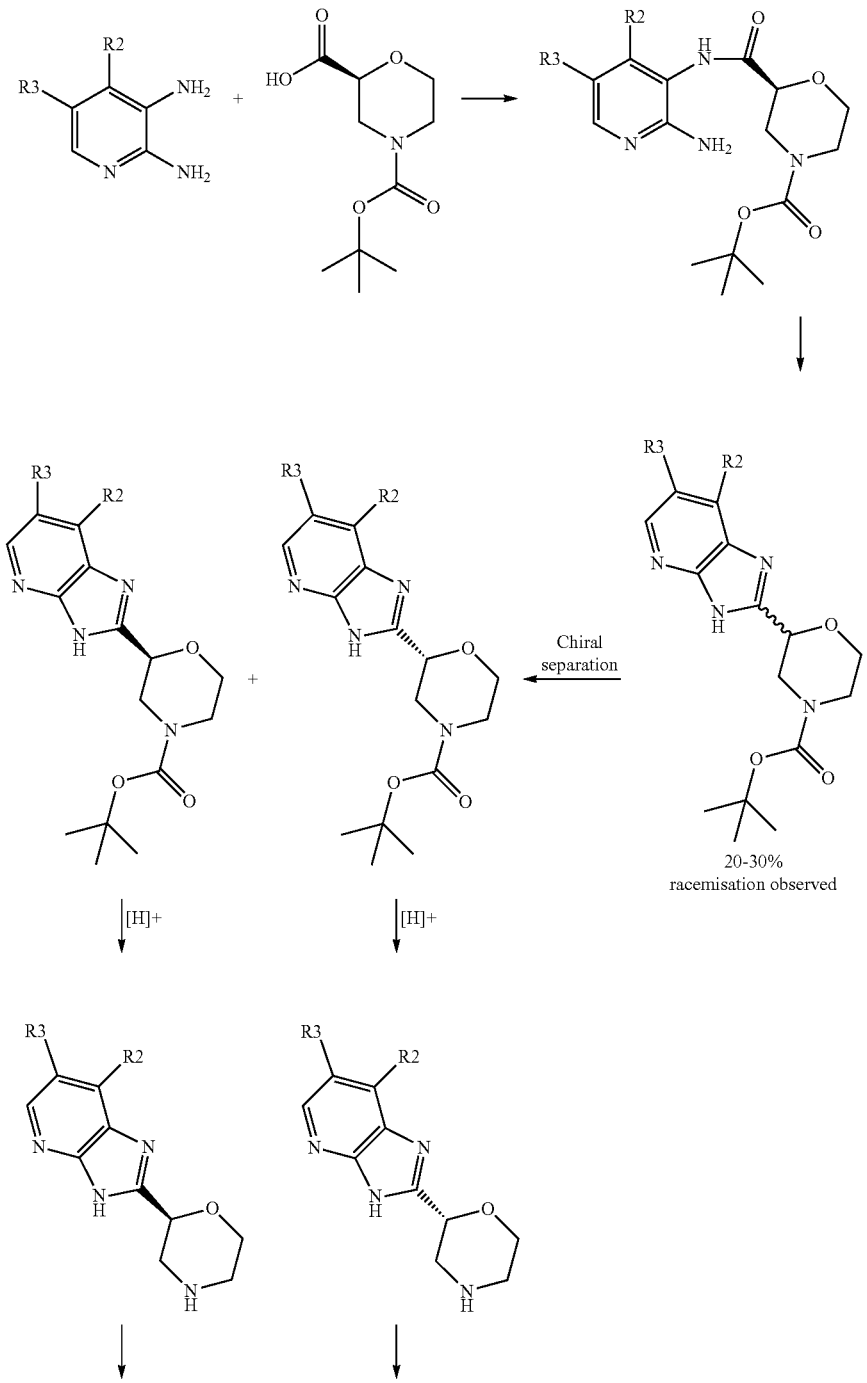

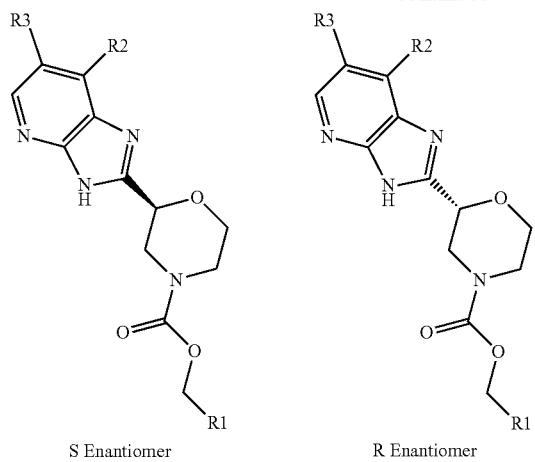
S Enantiomer    R Enantiomer
Scheme 2
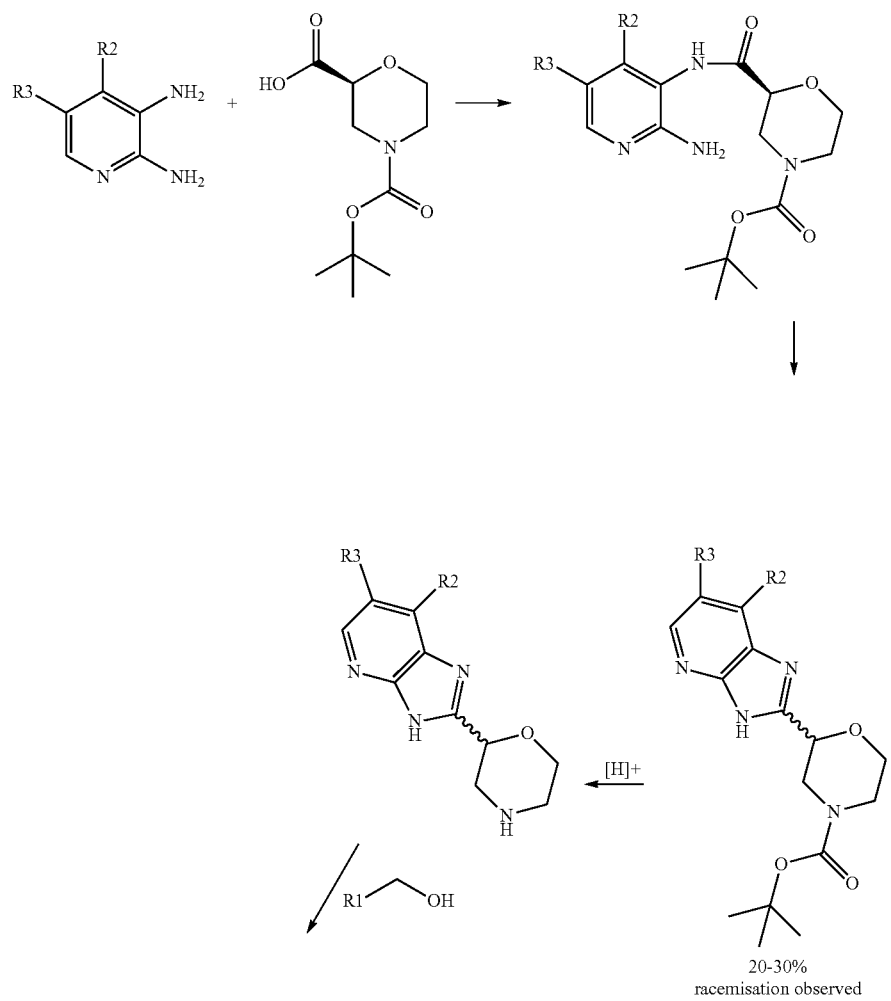
20-30% racemisation observed

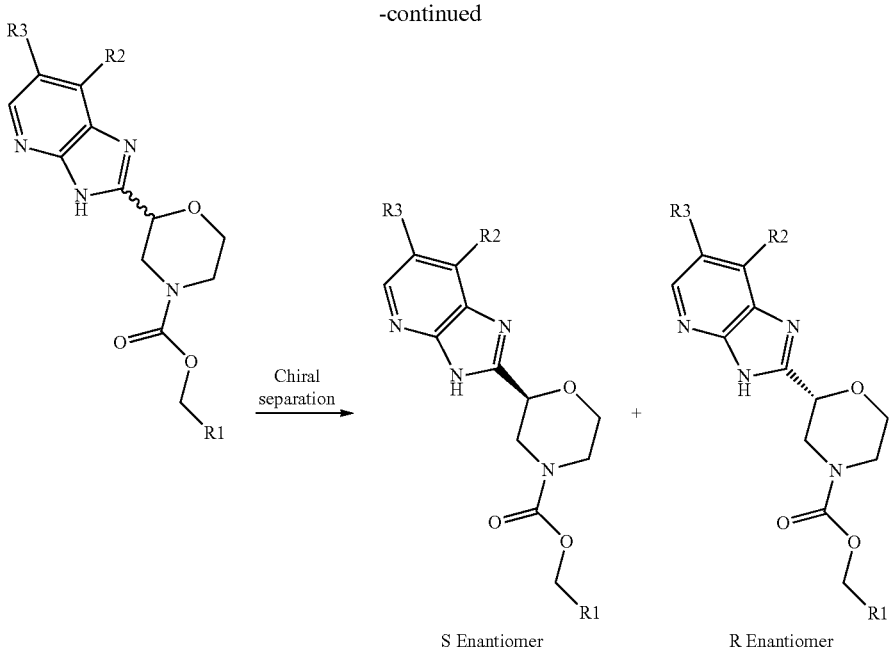

Alternatively, the synthesis according to schemes 1 and 2 can be performed using racemic morpholine-2,4-dicarboxylic acid 4-tert-butyl ester as starting material.

Both scheme 1 and 2 can be successfully used for gram scale synthesis of the final compounds starting from 40 mmoles of the desired substituted morpholine (racemic or the S enantiomer; Examples 3b, 3d, 3e according to the Experimental Section), using an excess of the desired substituted benzyl alcohol, DIPEA (3 equivalents), the needed coupling agent such as CDI and DMF as solvent.

An alternative gram scale synthesis can be performed using the corresponding morpholine (racemic or the S enantiomer; 40 mmol), TEA (2.5 equivalents), a slight excess of the required imidoylcarbonate and a 1/1 mixture CH₃CN/THF as solvent.

In scheme 1 and 2 all substituents $R^1$, $R^2$ and $R^3$ have the meaning as defined for general formula A, all embodiments of the invention that directly refer thereto and specifically the meaning as defined in the claims.

General Definitions

Terms not specifically defined herein should be given the meanings that would be given to them by one skilled in the art in light of the disclosure and the context.

In case a compound of the present invention is depicted in form of a chemical name as well as a formula, the formula shall prevail in case of any discrepancy.

An asterisk may be used in sub-formulas to indicate the bond which is connected to the core molecule or to the substituent to which it is bound as defined.

The term "substituted" as used herein means that any one or more hydrogens on the designated atom is replaced with a selection from the indicated group, provided that the designated atom's viable valence number is not exceeded, and that the substitution results in a stable compound.

Stereochemistry:

Unless specifically indicated, throughout the specification and the appended claims, a given chemical formula or name shall encompass rotamers, tautomers and all stereo, optical and geometrical isomers (e.g. enantiomers, diastereoisomers, E/Z isomers etc.) and racemates thereof, as well as mixtures in different proportions of the separate enantiomers, mixtures of diastereoisomers, or mixtures of any of the foregoing forms where such isomers and enantiomers exist, as well as salts, including pharmaceutically acceptable salts thereof.

General formula A

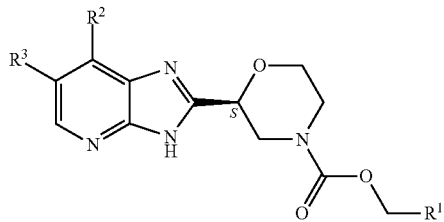

comprises both tautomers A-1 and A-2:

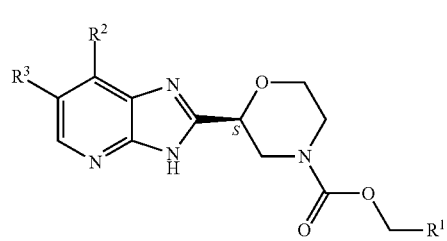

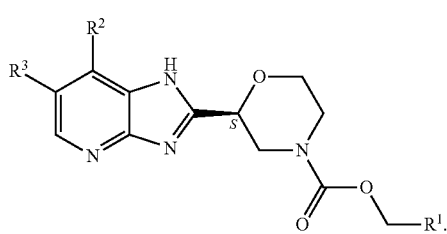

All compounds of the present invention exist in their tautomeric forms A-1 and/or A-2.

Salts:

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound forms a salt or a complex with an acid or a base.

Examples for acids forming a pharmaceutically acceptable salt with a parent compound containing a basic moiety include mineral or organic acids such as benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid or tartaric acid.

Examples for cations and bases forming a pharmaceutically acceptable salt with a parent compound containing an acidic moiety include $Na^+$, $K^+$, $Ca^{2+}$, $Mg^{2+}$, $NH_4^+$, L-arginine, 2,2'-iminobisethanol, L-lysine, N-methyl-D-glucamine or tris(hydroxymethyl)-aminomethane.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof. Salts of other acids than those mentioned above which for example are useful for purifying or isolating the compounds of the present invention (e.g. trifluoroacetate salts) also comprise a part of the invention.

Biological Assays and Data

LIST OF ABBREVIATIONS

BCRP Breast cancer resistance protein
DMEM Dulbecco's Modified Eagle's Medium
FBS fetal Bovine Serum
FLIPR fluorometric imaging plate reader
HEK293 cell line derived from human embryonic kidney cells
HEPES hydroxyethyl-piperazineethane-sulfonic acid buffer
MDCK Madin-Darby canine kidney
MDR1 Multi drug resistance protein 1
p-GP p-Glycoprotein In-Vitro Effect:

Determination of In Vitro Pharmacological Activity

The activity of the compounds of the invention may be demonstrated using the following in vitro NMDA NR1/NR2b cell assays:

Method:

A human HEK293 cell line with tetracyclin-inducible expression of NMDA NR1/NR2B receptor was used as a test system for compound efficacy and potency. The cell line was purchased from ChanTest, Catalog # CT6121. Compound activity was determined by measuring the effect of compounds on intracellular calcium concentration induced by glycine/glutamate agonism in a FLIPRtetra system (Molecular Devices).

Cell Culture:

The cells were obtained as frozen cells in cryo-vials and stored until use at −150° C. Cells were grown in culture medium (DMEM/F12, 10% FBS, 5 µg/mL Blasticidin, 150 µg/mL Zeozin, 500 µg/mL Geneticin). It is important that density does not exceed 80% confluence. For sub-culturing the cells were detached from flasks by Versene. For the assay, cells were detached, washed twice with induction medium (DMEM/F12 without glutamine, 10% FBS, 2 µg/mL Tetracycline, 2 mM Ketamine) and seeded to 384 well pure coat amine plates (BD 359324, 50000 cells per well in 50 µl) 48 h prior to assay in induction medium.

Compound Preparation

The test compounds were dissolved in 100% DMSO at a concentration of 10 mM and in a first step diluted in DMSO to a concentration of 5 mM, followed by serial dilution steps in 100% DMSO. Dilution factor and number of dilution steps may vary according to needs. Typically 8 different concentrations by 1:5 dilutions were prepared in duplicate, further intermediate dilutions (1:37.5) of the substances were carried out with aqueous assay buffer (137 mM NaCl, 4 mM KCl, 1.8 mM CaCl, 10 mM HEPES, 10 mM Glucose, pH 7.4) resulting in a compound concentration 3 times above the final test concentration and DMSO at 2.7% resulting in 0.9% final DMSO concentration in the assay.

FLIPR Assay:

At the assay day cells were washed 3× with assay puffer, 10 µL buffer remained in the wells after washing. 10 µL Ca kit loading buffer (AAT Bioquest) was added to the cells and the plates were incubated with lid for 60 minutes at r.t. 20 µl assay buffer containing 60 µM glycine (20 µM final) and 3 µM glutamate (1 µM final) was added to column 1-23. Fluorescence (indicating the calcium influx as a result of the NR1/NR2B ion channel activation) was read on the FLIPRtetra device for 60 seconds to monitor the glutamate induced effects. After 2 minutes 20 µL of compound or controls (row 1-22) in assay buffer were carefully added to the wells. Fluorescence was read on the FLIPR tetra device for additional 6 minutes to monitor the compound induced effects after activation by agonists. The average of 2 measurements at 5 minutes and 5 min 10 seconds after compound addition is calculated and further used for IC50 calculations. Each assay microtiter plate contained wells (in column 23 or 24) with DMSO controls instead of compound as controls for glycine/glutamate induced fluorescence (high controls) and wells with 1 µM of a reference NR2b NAM as low controls (Compound 22; reference: Layton, Mark E et al, ACS Chemical Neuroscience 2011, 2(7), 352-362).

Data Evaluation and Calculation:

The output file of the reader contains the well number and measured average fluorescence units. For data evaluation and calculation, the measurement of the low control was set as 0% control and the measurement of the high control was set as 100% control. The IC50 values were calculated using the standard 4 parameter logistic regression formula. Calculation: $[y=(a-d)/(1+(x/c)^b)+d]$, a=low value, d=high value; x=conc M; c=IC50 M; b=slope.

NR2B negative allosteric modulators covered by general structure A and exhibiting a low $IC_{50}$ value are preferred.

TABLE 1

In vitro affinity of the compounds of the present invention as obtained in the FLIPR assay

| Example number | IC50 [nM] |
| --- | --- |
| 1 | 409 |
| 2 | 83 |
| 4 | 228 |
| 6 | 475 |
| 8 | 404 |
| 9 | 293 |
| 10 | 156 |
| 11 | 55 |
| 12 | 73 |
| 13 | 122 |
| 14 | 121 |
| 15 | 93 |
| 16 | 104 |
| 17 | 76 |
| 18 | 54 |
| 19 | 128 |
| 24 | 748 |
| 25 | 477 |
| 26 | 78 |
| 27 | 95 |
| 28 | 42 |
| 31 | 132 |

TABLE 2

In vitro affinity of the closest prior art compounds (examples 1734, 1744, 1745, 1757, 1758, 1785 and 1790 in WO2016/29146) as obtained in the same FLIPR assay as compounds in table 1

| Example number in WO2016/29146 | IC50 [nM] |
| --- | --- |
| 1734 | >8885 |
| 1744 | >8889 |
| 1745 | >8898 |
| 1757 | >8900 |
| 1758 | >8884 |
| 1785 | 6200 |
| 1790 | >8887 |

MDCK Assay MDR-1 (p-GP)

Apparent permeability coefficients (Papp) of the compounds across the MDCK-MDR1 monolayers (MDCKII cells transfected with human MDR1 cDNA expression plasmid) are measured in apical-to-basal (AB) and basal-to-apical (BA) direction.

MDCK-MDR1 cells ($6 \times 10^5$ cells/cm$^2$) are seeded on filter inserts (Corning, Transwell, polycarbonate, 0.4 µm pore size) and cultured for 9 to 10 days. Compounds dissolved in DMSO stock solution (1-20 mM) are diluted with HTP-4 aqueous buffer (128.13 mM NaCl, 5.36 mM KCl, 1 mM MgSO4, 1.8 mM CaCl2, 4.17 mM NaHCO3, 1.19 mM Na2HPO4, 0.41 mM NaH2PO4, 15 mM HEPES, 20 mM glucose, pH 7.4) supplemented with 0.25% BSA to prepare the transport solutions (final concentration: 1 or 10 µM, final DMSO <=0.5%). The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS. Sampled receiver volumes are replaced with fresh receiver solution. Efflux ratio is calculated dividing the Papp (b-a) values by the Papp (a-b) values. Results are shown in table 3.

TABLE 3

| Ex. | Papp (a-b) mean [10 − 6 cm/s] | efflux ratio |
| --- | --- | --- |
| 1 | 61 | 0.9 |
| 2 | 31.5 | 1.7 |
| 6 | 44.4 | 1.48 |
| 8 | 39 | 1.6 |
| 9 | 49 | 1.16 |
| 10 | 37 | 1.6 |
| 11 | 32 | 1.4 |
| 12 | 46 | 0.9 |
| 13 | 35 | 1.3 |
| 14 | 38 | 1.1 |
| 15 | 59 | 1.2 |
| 16 | 41 | 1.2 |
| 17 | 40 | 1.3 |
| 18 | 37 | 1.3 |
| 19 | 42 | 1.6 |
| 26 | 32 | 2 |
| 27 | 65 | 1.2 |
| 28 | 42 | 1.1 |
| 31 | 18 | 1.8 |

The experimental results above show that compounds of the present invention are potent NR2B NAMs having good membrane permeability and low to moderate in vitro efflux.

MDCK Assay BCRP

Apparent permeability coefficients (Papp) of the compounds across the MDCK-BCRP monolayers (MDCKII cells transfected with human BCRP cDNA expression plasmid) are measured in apical-to-basal (AB) and basal-to-apical (BA) direction. MDCK-BCRP cells ($6 \times 10^5$ cells/cm$^2$) are seeded on filter inserts (Corning, Transwell, polycarbonate, 0.4 µm pore size) and cultured for 9 to 10 days. Compounds dissolved in DMSO stock solution (1-20 mM) are diluted with HTP-4 aqueous buffer (128.13 mM NaCl, 5.36 mM KCl, 1 mM MgSO4, 1.8 mM CaCl2, 4.17 mM NaHCO3, 1.19 mM Na2HPO4, 0.41 mM NaH2PO4, 15 mM HEPES, 20 mM glucose, pH 7.4) supplemented with 0.25% BSA to prepare the transport solutions (final concentration: 1 or 10 µM, final DMSO <=0.5%). The transport solution is applied to the apical or basolateral donor side for measuring A-B or B-A permeability, respectively. The receiver side contains HTP-4 buffer supplemented with 0.25% BSA. Samples are collected at the start and end of experiment from the donor and at various time intervals for up to 2 hours also from the receiver side for concentration measurement by HPLC-MS/MS. Sampled receiver volumes are replaced with fresh receiver solution. Efflux ratio is calculated dividing the Papp (b-a) values by the Papp (a-b) values. Results are shown in Table 4.

TABLE 4

| Ex. | Papp (a-b) mean [10 − 6 cm/s] | efflux ratio |
| --- | --- | --- |
| 1 | 38 | 2.4 |
| 2 | 34 | 2.9 |
| 8 | 46 | 1.8 |
| 10 | 40 | 2.2 |
| 11 | 63 | 1 |
| 12 | 69 | 1 |
| 13 | 72 | 0.9 |
| 14 | 68 | 1.2 |
| 15 | 33 | 2.8 |
| 16 | 49 | 2.1 |
| 17 | 37 | 2.5 |
| 18 | 53 | 1.2 |
| 19 | 61 | 1.6 |
| 26 | 24 | 2.7 |

TABLE 4-continued

| Ex. | Papp (a-b) mean [10 − 6 cm/s] | efflux ratio |
|---|---|---|
| 27 | 24 | 5.2 |
| 28 | 56 | 1.2 |
| 31 | 85 | 0.7 |

Metabolic Stability

The metabolic degradation of the test compound was assayed at 37° C. with pooled human liver microsomes. The final incubation volume of 60 μl per time point contains TRIS buffer pH 7.6 at room temperature (0.1 M), magnesium chloride (5 mM aqueous solution), microsomal protein (1 mg/mL for human) and the test compound at a final concentration of 1 μM. Following a short preincubation period at 37° C., the reactions were initiated by addition of betanicotinamide adenine dinucleotide phosphate, reduced form (NADPH, 1 mM), and terminated by transferring an aliquot into solvent after different time points. After centrifugation (10000 g, 5 min), an aliquot of the supernatant was assayed by LC-MS/MS for the amount of parent compound. The half-life was determined by the slope of the semi-logarithmic plot of the concentration-time profile. Results are shown in Table 5.

TABLE 5

| Ex. | Half-life - $t^{1/2}$ [min] human liver microsomes |
|---|---|
| 1 | 38 |
| 2 | 76 |
| 4 | 24 |
| 6 | 40 |
| 8 | 14 |
| 9 | 22 |
| 10 | 12 |
| 11 | 24 |
| 12 | 36 |
| 13 | 37 |
| 14 | 27 |
| 15 | 86 |
| 16 | >130 |
| 17 | >130 |
| 18 | 51 |
| 19 | 130 |
| 26 | >130 |
| 27 | 130 |
| 28 | >130 |
| 31 | 16 |

The present invention provides compounds according to formula A that unexpectedly result in a favorable combination of the following key parameters:
1) NR2B negative allosteric modulation,
2) favorable stability in human liver microsomes, and
3) moderate to low in vitro efflux at both MDR1 and BCRP transporters.

Pharmaceutical Composition

Suitable preparations for administering the compounds of the present invention will be apparent to those with ordinary skill in the art and include for example tablets, pills, capsules, suppositories, lozenges, troches, solutions, syrups, elixirs, sachets, injectables, inhalatives, powders, etc. The content of the pharmaceutically active compound(s) may vary in the range from 0.1 to 95 wt.-%, preferably 5.0 to 90 wt.-% of the composition as a whole.

Suitable tablets may be obtained, for example, by mixing a compound of the present invention with known excipients, for example inert diluents, carriers, disintegrants, adjuvants, surfactants, binders and/or lubricants and pressing the resulting mixture to form tablets.

Use in Treatment/Method of Use

Human therapeutic applications of NR2B NAM have been summarized in reviews by Traynelis et al. (Traynelis et al., Pharmacology Reviews, 2010, 62:405), Beinat et al. (Beinat et al., Current Medicinal Chemistry, 2010, 17:4166) and Mony et al. (Mony et al., British J. Pharmacology, 2009, 157:1301).

The present invention relates to compounds which are useful in the treatment of psychiatric disorders, diseases and conditions wherein negative allosteric modulation of NR2B is of therapeutic benefit, including: (1) mood disorders and mood affective disorders; (2) schizophrenia spectrum disorders; (3) neurotic, stress-related and somatoform disorders including anxiety disorders; (4) disorders of psychological development; (5) behavioral syndromes associated with physiological disturbances and physical factors; (6) substance-related and addictive disorders; (7) disease associated with symptoms of negative and positive valence.

In view of their pharmacological effect, compounds of the present invention are suitable for use in the treatment of a disorder, disease or condition selected from the list consisting of (1) treatment of mood disorders and mood affective disorders including bipolar disorder I depressed, hypomanic, manic and mixed form; bipolar disorder II; depressive disorders, such as single depressive episode or recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, catatonia.

(2) treatment of mood disorders belonging to the schizophrenia spectrum and other psychotic disorders including schizophrenia and schizoaffective disorder with associated negative and cognitive symptoms.

(3) treatment of disorders belonging to the neurotic, stress-related and somatoform disorders including anxiety disorders, general anxiety disorder, panic disorder with or without agoraphobia, specific phobia, social phobia, chronic anxiety disorders; obsessive compulsive disorder; reaction to sever stress and adjustment disorders, such as post-traumatic stress disorder; other neurotic disorders such as depersonalisation-derealisation syndrome.

(4) treatment of disorders of psychological development including pervasive developmental disorders, including Asperger's syndrome and Rett's syndrome, autistic disorders, childhood autism and overactive disorder associated with mental retardation and stereotyped movements, specific developmental disorder of motor function, specific developmental disorders of scholastic skills, attention deficit/hyperactivity disorder.

(5) treatment of behavioral syndromes associated with physiological disturbances and physical factors including mental and behavioural disorders associated with the puerperium, including postnatal and postpartum depression; eating disorders, including anorexia nervosa and bulimia nervosa and other impulse control disorders.

(6) treatment of disorders of substance-related and addicitive disorders, which are substance use disorders induced by alcohol, *cannabis*, hallucinogen, stimulant, hypnotic, tobacco.

(7) treatment of disease associated with symptoms of negative and positive valence including anhedonia, sustained threat and loss, suicidal ideation.

As used herein, unless otherwise noted, the terms "treating", "treatment" shall include the management and care of a human subject or human patient for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

According to another aspect, the present invention provides a compound of formula A or a pharmaceutically acceptable salt thereof for use in the treatment and/or prevention of the above mentioned conditions.

According to another aspect, the present invention provides a compound of formula A according to any one of the preceding aspects characterized in that the compound of formula A is used in addition to behavioural therapy, TMS (transcranial magnetic stimulation), ECT (electroconvulsive therapy) and other therapies.

Combination Therapy

Compounds according to the present invention can be combined with other treatment options known to be used in the art in connection with a treatment of any of the indications the treatment of which is in the focus of the present invention.

According to another aspect, the present invention provides a compound of formula A according to any one of the preceding aspects characterized in that the compound of formula A is administered in addition to treatment with one or more antidepressant selected from the list consisting of duloxetine, escitalopram, bupropion, venlafaxine, desvenlafaxine, sertraline, paroxetine, fluoxetine, vortioxetine, mirtazapine, citalopram, vilazodone, trazodone, amitriptyline, clomipramine, agomelatine, levomilnacipran, lithium, doxepin, nortriptyline. The term "antidepressant" shall mean any pharmaceutical agent or drug which can be used to treat depression or diseases associated with depressive symptoms. According to another aspect, the present invention provides a compound of formula A according to any one of the preceding aspects characterized in that the compound of formula A is administered in addition to treatment with one or more antipsychotic selected from the list consisting of aripiprazole, paliperidone palmitate, lurasidone, quetiapine, risperidone, olanzapine, paliperidone, brexpiprazole, clozapine, asenapine, chlorpromazine, haloperidol, cariprazine, ziprasidone, amisulpride, iloperidone, fluphenazine, blonanserin, aripiprazole lauroxil. The term "antipsychotic" shall mean any pharmaceutical agent or drug which can be used to treat diseases associated with psychotic or depressive symptoms.

According to another aspect, the present invention provides a compound of formula A according to any one of the preceding aspects characterized in that the compound of formula A is administered in addition to treatment with one or more psychostimulant selected from the list consisting of lisdexamfetamine, methylphenidate, amfetamine, dexamfetamine, dexmethylphenidate, armodafinil, modafinil. The term "psychostimulant" shall mean any pharmaceutical agent or drug which can be used to treat diseases like mood disorders, or impulse control disorders.

According to another aspect, the present invention provides a compound of formula A according to any one of the preceding aspects characterized in that the compound of formula A is administered in addition to treatment with nootropics selected from the list consisting of oxiracetam, piracetam, or the natural product St John's-wort.

According to another aspect, the present invention provides a compound of formula A which is administered in addition to treatment with one or more antidepressant, antipsychotic, psychostimulant, nootropics or natural product according to any one of the preceding aspects characterized in that the combination of compound of formula A and one or more antidepressant, antipsychotic, psychostimulant, nootropics or natural product is used in addition to behavioural therapy, TMS (transcranial magnetic stimulation), ECT (electroconvulsive therapy) and other therapies.

EXPERIMENTAL SECTION

Abbreviations

ACN acetonitrile
APCI Atmospheric pressure chemical ionization
Boc tert-butyloxycarbony
CDI 1,1'-carbonyldiimidazole
CO2 Carbon Dioxide
d day
DCM dichloromethane
DIPE diisopropylether
DIPEA diisopropylethylamine
DMF dimethylformamide
ESI electrospray ionization (in MS)
EtOAc ethylacetate
EtOH ethanol
Exp. example
h hour(s)
HATU O-(7-azabenzotriazol-1-yl)-N,N,N',N'-tetramethyluroniumhexafluorophosphate HPLC high performance liquid chromatography
HPLC-MS coupled high performance liquid chromatography-mass spectrometry
M molar (mol/L)
MeOH methanol
min minute(s)
MS mass spectrometry
MW molecular weight
NH3 ammonia
PSI Pound per square inch
rt room temperature
$R_t$ retention time
scCO2 supercritical CO2
solv solvent
TBTU O-(benzotriazol-1-yl)-N,N,N',N'-tetramethyluronium tetrafluoroborate
TEA triethylamine
TFA trifluoroacetic acid
THF tetrahydrofuran
TLC thin-layer chromatography
SFC Supercritical fluid chromatography Abbreviations within Spectral Data 1H-NMR Proton nuclear magnetic resonance
br broad
δ chemical shift d doublet
dd doublet of doublets
dt doublet of triplets
DMSO-$d_6$ hexa-deutero-dimethylsulfoxide
H proton
Hz Hertz (=1/second)
J coupling constant
m multiplet
ppm parts per million
q quartet
s singlet
t triplet
td triplet of doublets General Analytics All reactions were carried out using commercial grade reagents and solvents. NMR spectra were recorded on a Bruker AVANCE IIIHD 400 MHz instrument using TopSpin 3.2 p16 software. Chemical shifts are given in parts per million (ppm) downfield from internal reference trimethylsilane in δ units. Selected data are reported in the following manner: chemical shift, multiplicity, coupling constants (J), integration. Analytical thin-layer chromatography (TLC) was carried out using Merck silica gel 60 F254 plates. All compounds were visualized as single spots using short wave UV light. Low resolution mass spectra were obtained using a liquid chromatography mass spectrometer (LCMS) that consisted of an Agilent 1100 series LC coupled to a Agilent 6130 quadrupole mass spectrometer (electrospray positive ionization).

Methods:
HPLC-Ms Methods:
Method 1

| Method Name: | Z003_S05 |
| --- | --- |
| Device description: | Agilent 1200 with DA- and MS-Detector |
| Column: | XBridge C18_3.0 × 30 mm_2.5 μm |
| Column producer: | Waters |
| Description: | |

| Gradient/ Solvent Time [min] | % Sol [Water 0.1% $NH_3$] | % Sol [Acetonitrile] | Flow [ml/min] | Temp [° C.] | Back pressure [PSI] |
| --- | --- | --- | --- | --- | --- |
| 0.0 | 95.0 | 5.0 | 2.2 | 60.0 | |
| 0.2 | 95.0 | 5.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method 2

| Method Name: | Z011_S03 |
| --- | --- |
| Device description: | Agilent 1200 with DA- and MS-Detector |
| Column: | XBridge C18_3.0 × 30 mm_2.5 μm |
| Column producer: | Waters |
| Description: | |

| Gradient/ Solvent Time [min] | % Sol [Water 0.1% $NH_3$] | % Sol [Acetonitrile] | Flow [ml/min] | Temp [° C.] | Back pressure [PSI] |
| --- | --- | --- | --- | --- | --- |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Method 3

| Method Name: | 004_CA10 |
| --- | --- |
| Device description: | Waters Acquity, QDa Detector |
| Column: | XBridge C18_3.0 × 30 mm_2.5 μm |
| Column producer: | Waters |
| Description: | |

| Gradient/ Solvent Time [min] | % Sol [Water 0.1% $NH_3$] | % Sol [Acetonitrile] | Flow [ml/min] | Temp [° C.] | Back pressure [PSI] |
| --- | --- | --- | --- | --- | --- |
| 0.0 | 95.0 | 5.0 | 1.5 | 60.0 | |
| 1.3 | 0.0 | 100.0 | 1.5 | 60.0 | |
| 1.5 | 0.0 | 100.0 | 1.5 | 60.0 | |
| 1.6 | 95.0 | 5.0 | 1.5 | 60.0 | |

Method 4

| Method Name: | Z018_S04 |
| --- | --- |
| Device description: | Agilent 1200 with DA- and MS-Detector |
| Column: | Sunfire C18_3.0 × 30 mm_2.5 μm |
| Column producer: | Waters |

| Gradient/ Solvent Time [min] | % Sol [Water 0.1% TFA] | % Sol [Acetonitrile] | Flow [ml/min] | Temp [° C.] | Back pressure [PSI] |
| --- | --- | --- | --- | --- | --- |
| 0.0 | 97.0 | 3.0 | 2.2 | 60.0 | |
| 0.2 | 97.0 | 3.0 | 2.2 | 60.0 | |
| 1.2 | 0.0 | 100.0 | 2.2 | 60.0 | |
| 1.25 | 0.0 | 100.0 | 3.0 | 60.0 | |
| 1.4 | 0.0 | 100.0 | 3.0 | 60.0 | |

Chiral SFC Analytical Methods:
Method 5:
I_C2_20_MeOH_$NH_3$_001

| Method Name: | I_C2_20_MEOH_$NH_3$_001 |
| --- | --- |
| Device description: | Agilent 1260 SFC with DAD and ELSD |
| Column: | Lux ® Cellulose-2_4.6 × 250 mm_5 μm |
| Column producer: | Phenomenex |

| Gradient/ Solvent Time [min] | % Sol [scCO2] | % Sol [MEOH 20 mM $NH_3$] | Flow [ml/min] | Temp [° C.] | Back pressure [PSI] |
| --- | --- | --- | --- | --- | --- |
| 0.0 | 80.0 | 20.0 | 4.0 | 40.0 | 2175.0 |
| 10.0 | 80.0 | 20.0 | 4.0 | 40.0 | 2175.0 |

Method 6:
I_C4_20_MeOH_$NH_3$_001

| Method Name: | I_C4_20_MEOH_$NH_3$_001 |
| --- | --- |
| Device description: | Agilent 1260 SFC with DAD and ELSD |
| Column: | Lux ® Cellulose-4_4.6 × 250 mm_5 μm |
| Column producer: | Phenomenex |

| Gradient/ Solvent Time [min] | % Sol [scCO2] | % Sol [MEOH 20 mM $NH_3$] | Flow [ml/min] | Temp [° C.] | Back pressure [PSI] |
| --- | --- | --- | --- | --- | --- |
| 0.0 | 80.0 | 20.0 | 4.0 | 40.0 | 2175.0 |
| 10.0 | 80.0 | 20.0 | 4.0 | 40.0 | 2175.0 |

Method 7: I_C4_30_MEOH_$NH_3$_001

| Method Name: | I_C4_30_MEOH_$NH_3$_001 |
| --- | --- |
| Device description: | Agilent 1260 SFC with DAD and ELSD |
| Column: | Lux ® Cellulose-4_4.6 × 250 mm_5 μm |
| Column producer: | Phenomenex |

-continued

| Gradient/ Solvent Time [min] | % Sol [scCO2] | % Sol [MEOH 20 mM NH₃] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

Method 8: I_IA_35_MEOH_NH₃_001

| Method Name: | I_IA_35_MEOH_NH₃_001 |
|---|---|
| Device description: | Agilent 1260 SFC with DAD and MS |
| Column: | Chiralpak ® IA_4.6 × 250 mm_5 µm |
| Column producer: | Daicel |

| Gradient/ Solvent Time [min] | % Sol [scCO2] | % Sol [MEOH 20 mM NH₃] | Flow [ml/min] | Temp [° C.] | Back pressure [PSI] |
|---|---|---|---|---|---|
| 0.0 | 65.0 | 35.0 | 4.0 | 40.0 | 2175.0 |
| 10.0 | 65.0 | 35.0 | 4.0 | 40.0 | 2175.0 |

Method 9: I_C4_30_ETOH_NH₃_001

| Method Name: | I_C4_30_ETOH_NH₃_001 |
|---|---|
| Device description: | Agilent 1260 SFC with DAD and ELSD |
| Column: | Lux ® Cellulose-4_4.6 × 250 mm_5 µm |
| Column producer: | Phenomenex |

| Gradient/ Solvent Time [min] | % Sol [scCO2] | % Sol [ETOH 20 mM NH₃] | Flow [ml/min] | Temp [° C.] | Back pressure [PSI] |
|---|---|---|---|---|---|
| 0.0 | 70.0 | 30.0 | 4.0 | 40.0 | 2175.0 |
| 10.0 | 70.0 | 30.0 | 4.0 | 40.0 | 2175.0 |

Method 10: LIG_40_MEOH_NH₃_001

| Method Name: | I_IG_40_MEOH_NH₃_001 |
|---|---|
| Device description: | Agilent 1260 SFC with DAD and MS |
| Column: | Chiralpak ®-IG_4.6 × 250 mm_5 µm |
| Column producer: | Daicel |

| Gradient/ Solvent Time [min] | % Sol [scCO2] | % Sol [ETOH 20 mM NH₃] | Flow [ml/min] | Temp [° C.] | Back pressure [PSI] |
|---|---|---|---|---|---|
| 0.0 | 60.0 | 40.0 | 4.0 | 40.0 | 2175.0 |
| 10.0 | 60.0 | 40.0 | 4.0 | 40.0 | 2175.0 |

Method 11: I_SA_15_MEOH_NH₃_001

| Method Name: | I_SA_15_MEOH_NH₃_001 |
|---|---|
| Device description: | Agilent 1260 SFC with DAD and MS |
| Column: | CHIRAL ART ® Amylose SA_4.6 × 250 mm_5 µm |
| Column producer: | YMC |

| Gradient/ Solvent Time [min] | % Sol [scCO2] | % Sol [ETOH 20 mM NH₃] | Flow [ml/min] | Temp [° C.] | Back pressure [PSI] |
|---|---|---|---|---|---|
| 0.0 | 85.0 | 15.0 | 4.0 | 40.0 | 2175.0 |
| 10.0 | 85.0 | 15.0 | 4.0 | 40.0 | 2175.0 |

Preparation of Intermediates

Example 1a

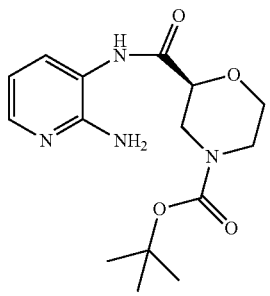 [SMILES: CC(C)(C)OC(=O)N1CCO[C@H](C(=O)Nc2cccnc2N)C1]

S-Morpholine-2,4-dicarboxylic acid 4-tertbutylester (10 g, 43.2 mmoles) was dissolved in DMF (120 ml) and the temperature was lowered to 0° C.; TBTU was then added and the mixture stirred 15 min before the addition of TEA (12.05 ml) and 2,3 Diammino pyridine (4.7 g; 43.2 mmoles). The reaction mixture was stirred 20 hours at room temperature before the work-up: DMF was removed under reduced pressure; the crude was diluted with EtOAc (300 ml) and water (100 ml) and then filtered with a glass filter. The organic phase was separated and washed with a 5% aqueous solution of sodium hydrogen carbonate (50 ml). The sodium hydrogen carbonate solution was back extracted with 100 ml of EtOAc, the organic phases combined together and dried over Na₂SO₄. The residue obtained after evaporation of the solvents was purified by flash chromatography using EtOAc/MeOH/NH₄OH (97/3/0.3).

Obtained 11.5 g

| HPLC-MS; Method: Z011_S03; R, [min]: 0.82 | MS: 323 (M + H)⁺ |
|---|---|
| Chiral SFC Rt Method: I_C2_20_MeOH_NH₃_001.M | Rt [min]: R-enantiomer 2.90; 4.7% (Area) |
| Chiral SFC Rt Method: I_C2_20_MeOH_NH₃_001.M | Rt [min]: S-enantiomer 3.38; 95.3% (Area) |

Example 1b

Example 1b was prepared in analogy to Example 1a. Starting materials: Morpholine-2,4 dicarboxylic acid 4-tert-butylester (550 mg, 2.4 mmol), 2,3 Diammino-5-fluoro-pyridine (340 mg; 2.7 mmol), TBTU (850 mg, 2.6 mmol) and TEA (1.0 mL, 7.2 mmol) in DMF (5 mL).

Obtained 580 mg

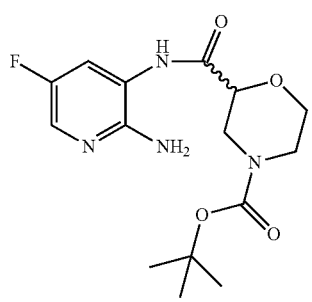

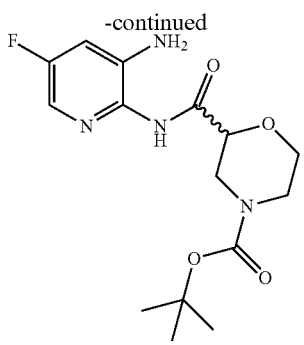

HPLC-MS; Method: Z018_S04; R$_t$ [min]: 0.79/0.87 MS: 323 (M+H)$^+$

Example 2a

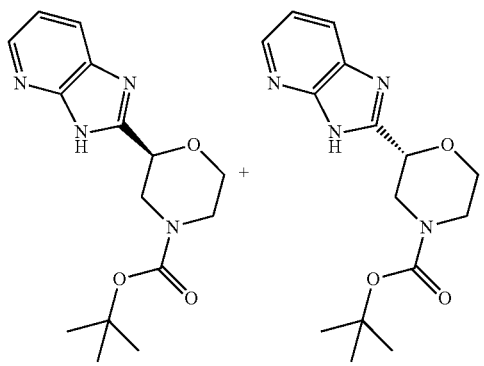

Example 1a (11.5 g, 35.67 mmoles) was dissolved in DMF (100 ml), CsF (7 g, 50 mmol) was added and the reaction mixture was stirred 28 hours at 100° C. The temperature was lowered at room temperature and DMF was removed under reduced pressure; the crude was partitioned with EtOAc (250 ml) and water (50 ml), the organic phase was separated and dried over Na$_2$SO$_4$. The crude obtained after evaporation of the solvent was purified by flash chromatography (DCM 95/MeOH 5/NH$_4$OH 0.5) to afford 5.2 g of the desired compound.

| HPLC-MS; Method: Z011_S03; R$_t$ [min]: 0.77 | MS: 305 (M + H)$^+$; 249 (M + H-Isobutene)$^+$ |
| --- | --- |
| Chiral SFC Rt Method: I_C2_20_MeOH_NH$_3$_001.M | Rt [min]: S-enantiomer 2.83; 81.75% |
| Chiral SFC Rt Method: I_C2_20_MeOH_NH$_3$_001.M | Rt [min]: R-enantiomer 3.63 min; 18.25% |

Analytical SFC indicated that a partial racemisation took place (e.e. 63.5%); 5.2 g were submitted to a chiral preparative SFC chromatography.

Preparative SFC Conditions:

| Column | Lux ®Cellulose-4_21.2 × 250 mm_5 μm |
| --- | --- |
| Solvents: | |
| scCO2 | 80% |
| MeOH 20 mM NH$_3$ | 20% |
| Backpressure regulator | 150 bar |
| Temperature | 40 |

| Flowrate | 60 ml/min |
| --- | --- |
| Sample concentration | 50 mg/ml |
| Sample solvent | MeOH |
| Injection Volume | 200 μl |
| Detector wavelength | 254 nM |
| Device | Jasco Rockclaw 150 |

Example 2b: Obtained 3.37 g after Preparative SFC Separation

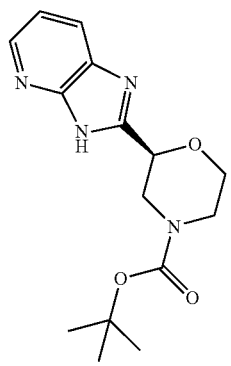 [SMILES: CC(C)(C)OC(=O)N1CCO[C@H](c2nc3cccnc3[nH]2)C1]

HPLC-MS; Method: Z011_S03; R$_t$ [min]: 0.76 MS: 305 (M+H)$^+$; 249 (M+H-Isobutene)$^+$ Rt [min]: 2.30

Chiral SFC Rt Method: I_C4_20_MeOH_NH$_3$_001. M $^1$H NMR (400 MHz, DMSO-d$_6$); δ ppm: 1.44 (s, 9H); 3.04 (br s, 1H); 3.17 (br s, 1H); 3.68 (td, J=11.43, 2.65 Hz, 1H); 3.82 (br d, J=13.39 Hz, 1H); 3.94-4.08 (m, 1H); 4.22 (br d, J=12.88 Hz, 1H); 4.76 (dd, J=10.23, 2.91 Hz, 1H); 7.22 (dd, J=7.83, 4.80 Hz, 1H); 7.93 (br d, J=7.58 Hz, 1H); 8.33 (dd, J=4.80, 1.26 Hz, 1H)

Example 2c: Obtained 0.75 g after Preparative SFC Separation

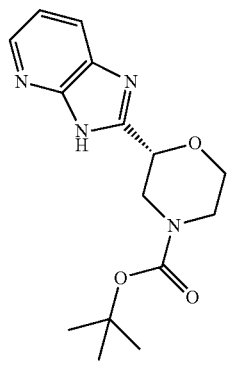 [SMILES: CC(C)(C)OC(=O)N1CCO[C@@H](c2nc3cccnc3[nH]2)C1]

HPLC-MS; Method: Z011_S03; R$_t$ [min]: 0.76 MS: 305 (M+H)$^+$; 249 (M+H-Isobutene)$^+$ R$_t$ [min]: 2.86

Chiral SFC; Method: I_C4_20_MeOH_NH$_3$_001. M $^1$H NMR (400 MHz, DMSO-d$_6$); δ ppm: 1.44 (s, 9H); 3.04 (br s, 1H); 3.17 (br s, 1H); 3.68 (td, J=11.43, 2.65 Hz, 1H); 3.82 (br d, J=13.39 Hz, 1H); 3.94-4.08 (m, 1H); 4.22 (br d, J=12.88 Hz, 1H); 4.76 (dd, J=10.23, 2.91 Hz, 1H);

7.22 (dd, J=7.83, 4.80 Hz, 1H); 7.93 (br d, J=7.58 Hz, 1H); 8.33 (dd, J=4.80, 1.26 Hz, 1H)

Example 2d

Example 1b (580 mg; 1.7 mmol) and $K_2CO_3$ (300 mg; 2.2 mmol) in 2-propanol (10 mL) were stirred at 80° C. for 6 h, at ambient temperature for 3 days and at reflux for 5 h. Then additional $K_2CO_3$ (300 mg; 2.2 mmol) was added and the mixture refluxed for 16 h. After cooling to room temperature, addition of ACN, and filtration, the mother liquid was evaporated and the residue purified by preparative HPLC (C-18 X-Bridge; 50° C.; $H_2O$+0.15% ammonia:acetonitrile=85:15->65:35) to obtain 440 mg of the desired product.

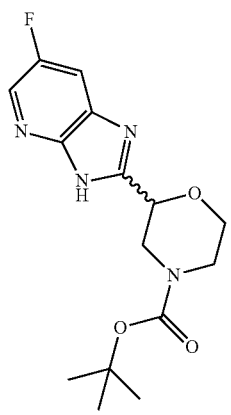 [SMILES: CC(C)(C)OC(=O)N1CCOC(c2nc3cc(F)cnc3[nH]2)C1]

HPLC-MS; Method: Z018_S04; $R_t$ [min]: 0.88 MS: 321 (M−H)$^-$; 267 (M+H-Isobutene)$^+$ Rt: 1.82 min (39.5%) and 2.48 min (60.5%)

Chiral SFC; Method: I_SA_15_MeOH_NH$_3$_001

$^1$H NMR (400 MHz, DMSO-d$_6$); δ ppm: 1.44 (s, 9H); 2.91-3.11 (m, 1H); 3.12-3.24 (m, 1H); 3.67 (td, J=11.44, 2.72 Hz, 1H); 3.81 (br d, J=13.31 Hz, 1H); 4.00 (br d, J=10.90 Hz, 1H); 4.21 (br d, J=12.55 Hz, 1H); 4.75 (dd, J=10.27, 3.04 Hz, 1H); 7.80-7.94 (m, 1H); 8.33 (s, 1H); 13.18 (br s, 1H)

Example 2e

A mixture from 2,3-diamino-4-methyl-pyridine (85 mg; 0.69 mmol), [(tert.-butoxy)carbonyl]morpholine-2-carboxylic acid (150 mg; 0.65 mmol), TBTU (220 mg; 0.69 mmol) and TEA (300 μl; 2.2 mmol) in DMF (2 mL) was stirred at ambient temperature for 30 min. Then acetic acid (2 mL) was added and the mixture stirred for 16 h at 100° C. After addition of dioxane it was freeze dried, the residue taken up in methanol, few drops of conc ammonia added, filtered and purified by preparative HPLC (C-18 X-Bridge; 50° C.; $H_2O$+0.15% ammonia:acetonitrile=82:18->62:38) to obtain 120 mg (58%) of the desired product.

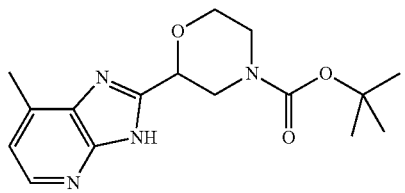 [SMILES: Cc1ccnc2[nH]c(C3CN(C(=O)OC(C)(C)C)CCO3)nc12]

HPLC-MS (Z011_S03): $R_t$ [min]: 0.80 MS: 319 (M+H)$^+$

Example 3b

Example 2b (1.3 g; 4.27 mmol) was dissolved in DCM (20 ml) and the reaction mixture was cooled at 0° C.; HCl (5.34 ml; 4N solution in Dioxane) was added and after 15 min the temperature was raised at rt. The reaction mixture was stirred 15 hours; the DCM was evaporated under reduced pressure at a temperature of 35° C.

Obtained 1.15 g of the desired product (Example 3b).

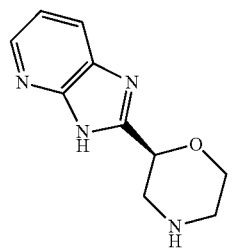 [SMILES: c1cnc2[nH]c([C@@H]3CNCCO3)nc2c1]

HPLC-MS; Method: Z011_S03; $R_t$ [min]: 0.18 MS: 205 (M+H)$^+$ $R_t$ [min]: 3.82

Chiral SFC Method: I_IA_35_MeOH_NH$_3$_001. M

Example 3d

Example 3d was prepared in analogy to Example 3b. Starting materials: Example 2d (440 mg, 1.4 mmol) and HCl (8 mL 1N solution in dioxane) in dioxane (4 mL).

Obtained: 400 mg

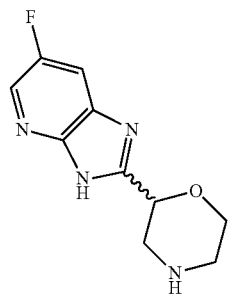 [SMILES: Fc1cnc2[nH]c(C3CNCCO3)nc2c1]

HPLC-MS; Method: Z011_S03; $R_t$ [min]: 0.16 MS: 223 (M+H)$^+$

Example 3e

Example 2e (120 mg; 0.69 mmol) was mixed with hydrogenchloride in dioxane (4N; 10 mL) and the mixture was stirred at ambient temperature for 16 h. The mixture was concentrated in vacuo and the residue (110 mg) used without further purification.

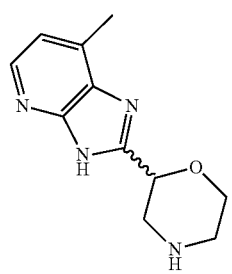 [SMILES: Cc1ccnc2[nH]c(C3CNCCO3)nc12]

HPLC-MS (Z011_503): $R_t$ [min]: 0.51 MS: 219 (M+H)$^+$

Example 4a

A mixture of (4-Fluoro-phenyl)-methanol (3.0 g, 23.8 mmol) and N,N'-disuccinimidyl carbonate (6.1 g, 23.8 mmol) with 4-Dimethylamino-pyridine (1.1 g, 9.0 mmol) in DCM (30 mL) and acetonitrile (30 mL) was stirred for 16 h at ambient temperature. After addition of more DCM, the mixture was extracted with water, hydrochloric acid (0.5 N) and aqueous Na$_2$CO$_3$ solution (1 N), the aqueous phases extracted with DCM, and the organic phases dried over MgSO4. After evaporation in vacuo, the residue was stirred with diethylether and concentrated. The resulting solid was again stirred with diethylether, filtrated, dried in vacuo and used without further purification. Amount obtained: 4.7 g.

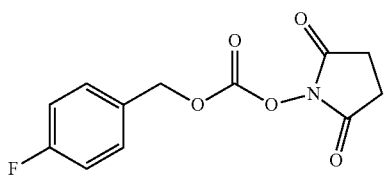 [SMILES: O=C(OCc1ccc(F)cc1)ON1C(=O)CCC1=O]

HPLC-MS (Method): Z018_S04 R$_t$ [min]: 0.94 MS: 267 (M+H)$^+$ $^1$H NMR (400 MHz, DMSO-d$_6$); δ ppm: 2.81 (s, 4H); 5.39 (s, 2H); 7.27 (t, J=8.30 Hz, 2H); 7.53 (t, J=6.46 Hz, 2H)

Example 4b

Example 4b was prepared in analogy to Example 4a. Starting materials: p-Tolyl-methanol (10.0 g, 81.9 mmol), N,N'-Disuccinimidyl carbonate (21.0 g, 81.6 mmol), 4-Dimethylaminopyridine (1.5 g, 12.3 mmol) in DCM (100 mL) with ACN (100 mL).

Obtained: 17.1 g

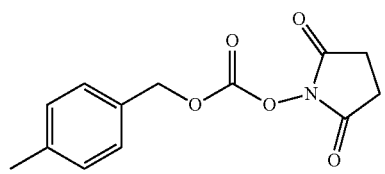 [SMILES: Cc1ccc(COC(=O)ON2C(=O)CCC2=O)cc1]

HPLC-MS (Method): Z018_S04 R$_t$ [min]: 0.98 MS: 296 (M+H+MeOH)$^+$ $^1$H NMR (400 MHz, DMSO-d$_6$); δ ppm: 2.32 (m, 3H); 2.80 (s, 4H); 5.34 (s, 2H); 7.24 (d, J=7.98 Hz, 2H); 7.34 (d, J=8.11 Hz, 2H)

Exemplary Embodiments

Example 1

(3-Fluoro-phenyl)-methanol (95.5 mg; 0.76 mmol) and CDI (123 mg; 0.76 mmol) were mixed together in DMF (3 ml); the reaction mixture was heated at 50° C. during 30 minutes; Example 3b (70 mg; 0.25 mmol) and DIPEA (0.13 ml; 0.76 mmol) were then added in sequence and the reaction mixture stirred 17 hours at 50° C. The reaction mixture was cooled to room temperature and the residue diluted with 1 ml of a mixture MeOH/Water (1/1) before being filtered and separated via semipreparative HPLC. Obtained 45 mg of the desired compound.

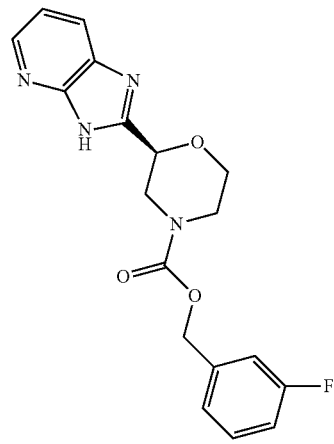 [SMILES: O=C(OCc1cccc(F)c1)N1CCO[C@H](c2nc3cccnc3[nH]2)C1]

HPLC-MS; Method: Z003_S05; R$_t$ [min]: 0.99 MS: 357 (M+H)$^+$ Rt [min]: 2.60

Chiral SFC; Method: I_C4_30_MEOH_NH$_3$_001

$^1$H NMR (400 MHz, DMSO-d$_6$); δ ppm: 3.02-3.23 (m, 1H); 3.73 (td, J=11.37, 2.72 Hz, 1H); 3.89 (br d, J=11.66 Hz, 1H); 4.02 (br d, J=11.41 Hz, 1H); 4.30 (br d, J=13.31 Hz, 1H); 4.84 (dd, J=10.01, 2.66 Hz, 1H); 5.12-5.20 (m, 2H); 7.13-7.27 (m, 4H); 7.43 (td, J=7.98, 6.21 Hz, 1H); 7.93 (br d, J=7.60 Hz, 1H); 8.33 (dd, J=4.75, 1.20 Hz, 1H); 13.01 (br s, 1H)

Example 2

Example 2 was prepared in analogy to Example 1. Starting materials: Example 3b (70 mg; 0.25 mmol), (4-Fluoro-phenyl)-methanol (82.3 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained: 50 mg

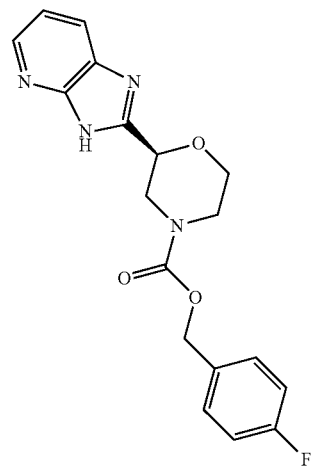 [SMILES: O=C(OCc1ccc(F)cc1)N1CCO[C@H](c2nc3cccnc3[nH]2)C1]

HPLC-MS: Method: Z003_S05; R$_t$ [min]: 0.98 MS: 357 (M+H)$^+$ Rt [min]; 2.61

Chiral SFC Method: I C4_30_EtOH_NH$_3$ 001

$^1$H NMR (400 MHz, DMSO-d$_6$); δ ppm: 3.03-3.22 (m, 1H); 3.67-3.77 (m, 1H); 3.87 (br d, J=13.64 Hz, 1H); 4.01 (br d, J=11.37 Hz, 1H); 4.28 (br d, J=12.63 Hz, 1H); 4.82 (dd, J=10.11, 2.78 Hz, 1H); 5.09-5.16 (m, 2H); 7.17-7.24 (m, 3H); 7.47 (dd, J=8.46, 5.68 Hz, 2H); 7.93 (br d, J=6.82 Hz, 1H); 8.33 (d, J=3.79 Hz, 1H); 12.99 (br s, 1H)

Example 4

Example 4 was prepared in analogy to Example 1. Starting materials: Example 3b (70 mg; 0.25 mmol), (4-Fluoro-2-methyl-phenyl)-methanol (106 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained: 35 mg

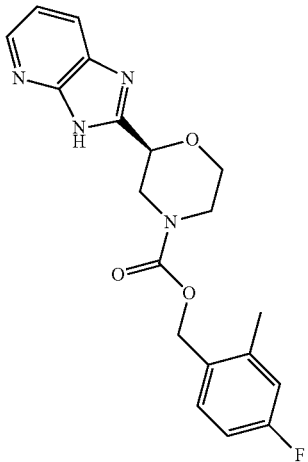 [SMILES: Cc1cc(F)ccc1COC(=O)N1CCO[C@H](c2nc3cccnc3[nH]2)C1]

HPLC-MS: Method: Z003_S05; $R_t$ [min]: 1.04 MS: 371 $(M+H)^+$ Rt [min]: 2.58

Chiral SFC; Method: I C4_30_MeOH_NH$_3$_001

$^1$H NMR (400 MHz, DMSO-d$_6$); δ ppm: 2.34 (s, 3H); 3.04-3.21 (m, 1H); 3.71 (br t, J=10.39 Hz, 1H); 3.85 (br d, J=13.31 Hz, 1H); 4.01 (br d, J=11.15 Hz, 1H); 4.25 (br s, 1H); 4.81 (dd, J=10.08, 2.98 Hz, 1H); 5.08-5.16 (m, 2H); 6.98-7.11 (m, 2H); 7.22 (dd, J=7.98, 4.82 Hz, 1H); 7.39 (dd, J=8.36, 6.21 Hz, 1H); 7.92 (br d, J=7.48 Hz, 1H); 8.32 (dd, J=4.69, 1.14 Hz, 1H); 13.00 (br s, 1H)

Example 5

A mixture from the product of example 3e (50 mg; 0.17 mmol), example 4a (50 mg; 0.19 mmol), and TEA (100 µl; 0.72 mmol) in THF (4 mL) and acetonitrile (4 mL) was heated to reflux and stirred at ambient temperature without further heating for 30 min. The mixture was concentrated in vacuo and the residue purified by preparative HPLC to obtain 35.7 mg of the desired product.

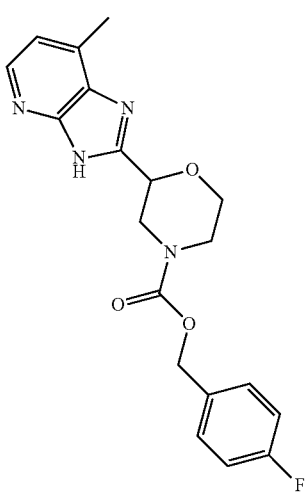 [SMILES: Cc1ccnc2[nH]c(C3CN(C(=O)OCc4ccc(F)cc4)CCO3)nc12]

HPLC-MS (004_CA10): $R_t$ [min]: 0.65 MS: 371 $(M+H)^+$ $^1$H NMR (400 MHz, DMSO-d$_6$); δ ppm: 2.52-2.55 (m, 3H); 2.99-3.22 (m, 1H); 3.45-3.77 (m, 2H); 3.88 (br d, J=13.56 Hz, 1H); 4.01 (br d, J=11.53 Hz, 1H); 4.26 (br d, J=12.29 Hz, 1H); 4.79 (dd, J=10.20, 2.85 Hz, 1H); 5.08-5.17 (m, 2H); 7.04 (dd, J=4.82, 0.63 Hz, 1H); 7.20 (t, J=8.36 Hz, 2H); 7.46 (t, J=6.13 Hz, 2H); 8.18 (d, J=4.82 Hz, 1H)

A sample of the product of example 5 (34 mg) was separated by chiral chromatography (SFC) to get access to Ex. 6.

Preparative Conditions:

| Column | Chiralpak® IG_10 × 250 mm_5 µm |
|---|---|
| Solvents: | |
| scCO2 | 60% |
| MeOH 20 mM NH$_3$ | 40% |
| Backpressure regulator | 120 bar |
| Temperature | 40° C. |
| Flowrate | 10 ml/min |
| Sample concentration | 6 mg/ml |
| Sample solvent | MeOH:DCM 1:1 |
| Injection Volume | 300 µl |
| Detector wavelength | 220 nm |
| Device | Mini Gram |

Example 6

Obtained: 16 mg

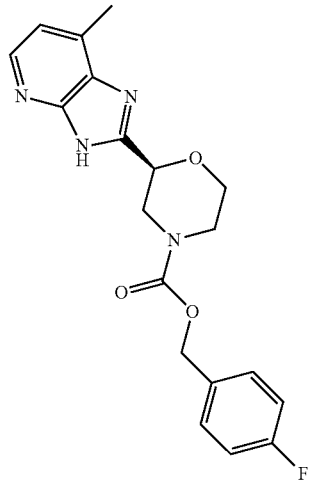 [SMILES: Cc1ccnc2[nH]c([C@@H]3CN(C(=O)OCc4ccc(F)cc4)CCO3)nc12]

Chiral SFC Method: IG_40_MEOH_NH$_3$_001 $R_t$: 3.61 min $^1$H NMR (400 MHz, DMSO-d$_6$); δ ppm: 2.52-2.54 (m, 3H); 3.08-3.25 (m, 1H); 3.35-3.47 (m, 1H); 3.71 (br t, J=10.61 Hz, 1H); 3.88 (br d, J=13.14 Hz, 1H); 4.01 (br d, J=10.86 Hz, 1H); 4.26 (br d, J=11.87 Hz, 1H); 4.79 (br d, J=8.34 Hz, 1H); 5.09-5.16 (m, 2H); 7.03 (d, J=4.80 Hz, 1H); 7.20 (t, J=8.84 Hz, 2H); 7.46 (dd, J=8.46, 5.68 Hz, 2H); 8.18 (br d, J=4.04 Hz, 1H); 12.98 (br s, 1H)

Example 8

Example 8 was prepared in analogy to Example 1. Starting materials: Example 3b (70 mg; 0.25 mmol), o-Tolyl-methanol (92.6 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 38 mg.

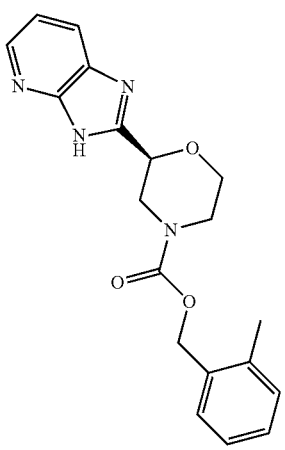 [SMILES: Cc1ccccc1COC(=O)N1CCO[C@H](c2nc3cccnc3[nH]2)C1]

HPLC-MS: Method: Z003_S05; $R_t$ [min]: 1.03 MS: 353 (M+H)$^+$ Rt [min]: 3.14

Chiral SFC Method: I C4_30_MeOH_NH$_3$_001

$^1$H NMR (400 MHz, DMSO-d$_6$); δ ppm: 2.32 (s, 3H); 3.03-3.22 (m, 1H); 3.66-3.78 (m, 1H); 3.87 (br d, J=13.56 Hz, 1H); 4.01 (br d, J=11.41 Hz, 1H); 4.17-4.37 (m, 1H); 4.82 (dd, J=10.08, 2.98 Hz, 1H); 5.15 (d, J=1.77 Hz, 2H); 7.17-7.27 (m, 4H); 7.34 (d, J=7.35 Hz, 1H); 7.92 (br d, J=7.48 Hz, 1H); 8.32 (dd, J=4.63, 1.08 Hz, 1H); 13.00 (br s, 1H)

Example 9

Example 9 was prepared in analogy to Example 1. Starting materials: Example 3b (70 mg; 0.25 mmol), m-Tolyl-methanol (91.2 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained 49 mg.

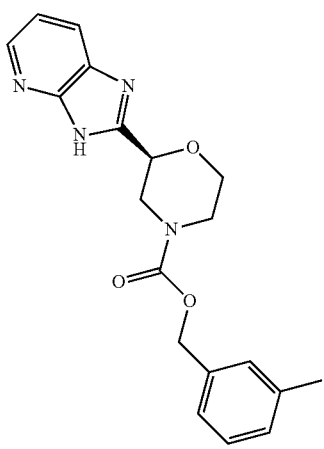 [SMILES: Cc1cccc(COC(=O)N2CCO[C@H](c3nc4cccnc4[nH]3)C2)c1]

HPLC-MS (Method): Z003_S05; $R_t$ [min]: 1.04; MS: 353 (M+H)$^+$ $R_t$ [min]: 3.17

Chiral SFC Method: I C4_30_MeOH_NH$_3$_001

$^1$H NMR (400 MHz, DMSO-d$_6$); δ ppm: 2.30-2.40 (m, 3H); 3.00-3.22 (m, 1H); 3.41-3.76 (m, 1H); 3.88 (br d, J=13.56 Hz, 1H); 4.02 (br d, J=11.15 Hz, 1H); 4.29 (br d, J=13.18 Hz, 1H); 4.82 (dd, J=10.14, 2.91 Hz, 1H); 5.06-5.14 (m, 2H); 7.13-7.29 (m, 5H); 7.92 (br d, J=7.48 Hz, 1H); 8.32 (dd, J=4.69, 1.14 Hz, 1H); 13.00 (br s, 1H)

Example 10

Example 10 was prepared in analogy to Example 1. Starting materials: Example 3b (70 mg; 0.25 mmol), (2-Fluoro-6-methyl-phenyl)-methanol (106 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 25 mg.

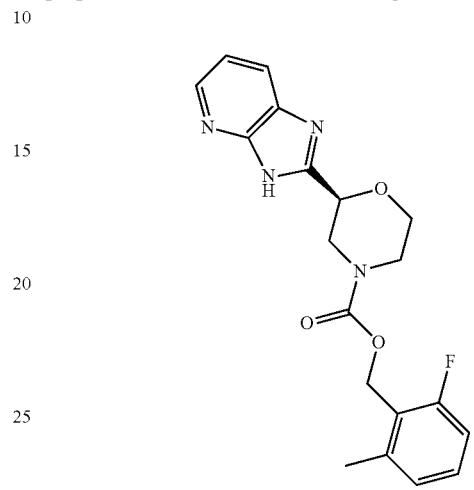

HPLC-MS (Method): Z003_S05; $R_t$ [min]: 1.03 MS: 371 (M+H)$^+$ $R_t$ [min]: 2.68

Chiral SFC Method: I C4_20_MeOH_NH$_3$_001

$^1$H NMR (400 MHz, DMSO-d$_6$); δ ppm: 2.40 (s, 3H); 3.03-3.20 (m, 1H); 3.61-3.76 (m, 1H); 3.82 (br s, 1H); 3.98 (br s, 1H); 4.18 (br s, 1H); 4.79 (br d, J=7.86 Hz, 1H); 5.17-5.23 (m, 2H); 7.03-7.12 (m, 2H); 7.21 (dd, J=7.92, 4.75 Hz, 1H); 7.32 (td, J=7.86, 6.21 Hz, 1H); 7.92 (br d, J=6.72 Hz, 1H); 8.32 (br d, J=4.06 Hz, 1H); 12.98 (br s, 1H)

Example 11

Example 11 was prepared in analogy to Example 1. Starting materials: Example 3b (70 mg; 0.25 mmol), (2-Fluoro-4-methyl-phenyl)-methanol (106 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 49 mg.

HPLC-MS (Method): Z003_S05; $R_t$ [min]: 1.06 MS: 371 (M+H)$^+$ $R_t$ [min]: 2.89

Chiral SFC Method: I C4_30_MeOH_NH$_3$_001

$^1$H NMR (400 MHz, DMSO-d$_6$); δ ppm: 2.25-2.34 (m, 3H); 3.01-3.20 (m, 1H); 3.39-3.75 (m, 1H); 3.76-3.91 (m, 1H); 4.01 (br d, J=9.76 Hz, 1H); 4.16-4.35 (m, 1H); 4.80 (dd, J=10.27, 2.91 Hz, 1H); 5.10-5.19 (m, 2H); 7.00-7.12 (m, 2H); 7.22 (dd, J=7.98, 4.69 Hz, 1H); 7.37 (t, J=7.86 Hz, 1H); 7.92 (br d, J=7.35 Hz, 1H); 8.32 (dd, J=4.63, 1.08 Hz, 1H); 13.00 (br s, 1H)

Example 12

Example 12 was prepared in analogy to Example 1. Starting materials: Example 3b (70 mg; 0.25 mmol), (3-Fluoro-4-methyl-phenyl)-methanol (106 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained 38 mg.

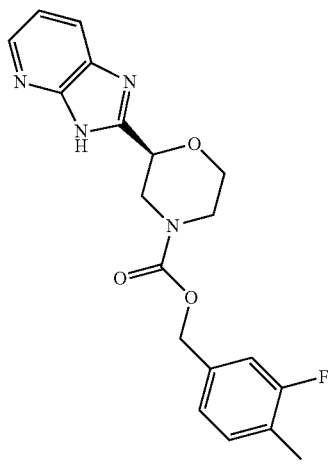 [SMILES: Cc1ccc(COC(=O)N2CCO[C@H](c3nc4cccnc4[nH]3)C2)cc1F]

HPLC-MS Method): Z003_S05; $R_t$ [min]: 1.06 MS: 371 (M+H)$^+$ $R_t$ [min]: 2.85

Chiral SFC Method: I C4_30_MeOH_NH$_3$_001

$^1$H NMR (400 MHz, DMSO-d$_6$); δ ppm: 2.23 (s, 3H); 3.05-3.25 (m, 1H); 3.72 (td, J=11.31, 2.65 Hz, 1H); 3.88 (br d, J=13.14 Hz, 1H); 4.01 (br d, J=11.12 Hz, 1H); 4.28 (br d, J=13.39 Hz, 1H); 4.82 (dd, J=10.10, 2.78 Hz, 1H); 5.06-5.15 (m, 2H); 7.12-7.31 (m, 4H); 7.93 (br d, J=7.33 Hz, 1H); 8.33 (d, J=3.54 Hz, 1H); 12.99 (br s, 1H)

Example 13

Example 13 was prepared in analogy to Example 1. Starting materials: Example 3b (70 mg; 0.25 mmol), (2-Chloro-4-fluoro-phenyl)-methanol (121.7 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 52 mg.

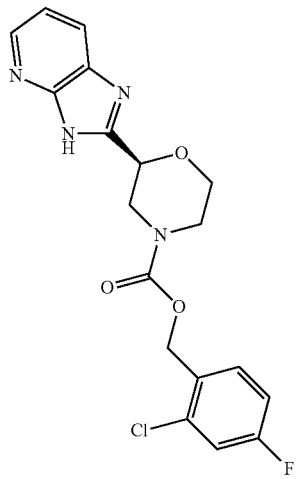 [SMILES: O=C(OCc1ccc(F)cc1Cl)N1CCO[C@H](c2nc3cccnc3[nH]2)C1]

HPLC-MS (Method): Z003_S05; $R_t$ [min]: 1.06 MS: 391 (M+H)$^+$ $R_t$ [min]: 2.81

Chiral SFC Method: I C4_30_MeOH_NH$_3$_001

$^1$H NMR (400 MHz, DMSO-d$_6$); δ ppm: 3.07-3.25 (m, 2H); 3.67-3.78 (m, 1H); 3.86 (br d, J=13.14 Hz, 1H); 4.01 (br d, J=11.12 Hz, 1H); 4.26 (br d, J=13.39 Hz, 1H); 4.83 (dd, J=9.98, 2.65 Hz, 1H); 5.15-5.23 (m, 2H); 7.20-7.29 (m, 2H); 7.50 (dd, J=8.84, 2.53 Hz, 1H); 7.61 (t, J=6.91 Hz, 1H); 7.92 (br d, J=7.83 Hz, 1H); 8.33 (d, J=3.54 Hz, 1H); 13.01 (br s, 1H)

Example 14

Example 14 was prepared in analogy to Example 1. Starting materials: Example 3b (70 mg; 0.25 mmol), (2-Chloro-phenyl)-methanol (108 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 54 mg.

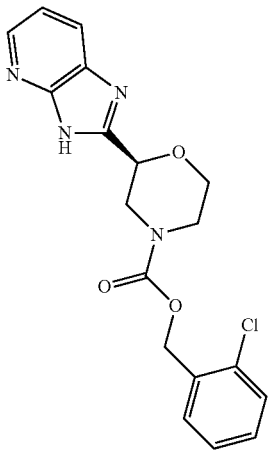 [SMILES: O=C(OCc1ccccc1Cl)N1CCO[C@H](c2nc3cccnc3[nH]2)C1]

HPLC-MS Method: Z003_S05; $R_t$ [min]: 1.04 MS: 373 (M+H)$^+$ $R_t$ [min]: 3.46

Chiral SFC Method: I C4_30_MeOH_NH₃_001

¹H NMR (400 MHz, DMSO-d₆); δ ppm: 3.04-3.24 (m, 1H); 3.73 (td, J=11.31, 2.47 Hz, 1H); 3.89 (br d, J=13.18 Hz, 1H); 4.02 (br d, J=11.41 Hz, 1H); 4.29 (br d, J=13.05 Hz, 1H); 4.84 (dd, J=10.08, 2.72 Hz, 1H); 5.17-5.27 (m, 2H); 7.22 (dd, J=7.98, 4.69 Hz, 1H); 7.35-7.43 (m, 2H); 7.46-7.58 (m, 2H); 7.93 (br d, J=7.48 Hz, 1H); 8.33 (dd, J=4.63, 1.08 Hz, 1H); 13.01 (br s, 1H)

Example 15

Example 15 was prepared in analogy to Example 1. Starting materials: Example 3b (70 mg; 0.25 mmol), (2,3-Difluoro-phenyl)-methanol (85.2 μl mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 50 mg.

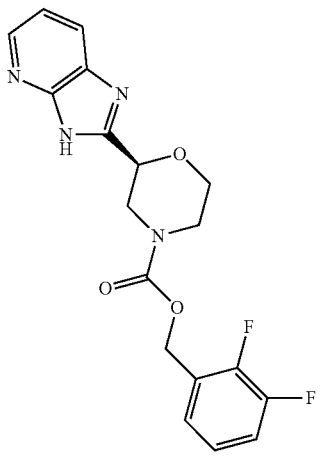 [SMILES: O=C(OCc1cccc(F)c1F)N1CCO[C@H](c2nc3cccnc3[nH]2)C1]

HPLC-MS Method: Z003_S05; R_t [min]: 1.00 MS: 375 (M+H)⁺ R_t [min]: 2.36

Chiral SFC Method: I C4_30_MeOH_NH₃_001

¹H NMR (400 MHz, DMSO-d₆); δ ppm: 3.04-3.23 (m, 1H); 3.72 (br t, J=10.33 Hz, 1H); 3.86 (br d, J=13.56 Hz, 1H); 4.01 (br d, J=11.15 Hz, 1H); 4.27 (br d, J=12.42 Hz, 1H); 4.83 (dd, J=10.14, 2.79 Hz, 1H); 5.19-5.29 (m, 2H); 7.20-7.47 (m, 4H); 7.93 (br d, J=7.48 Hz, 1H); 8.33 (dd, J=4.63, 0.95 Hz, 1H); 13.01 (br s, 1H)

Example 16

Example 16 was prepared in analogy to Example 1. Starting materials: Example 3b (70 mg; 0.25 mmol), (2,6-Difluoro-phenyl)-methanol (84 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 56 mg.

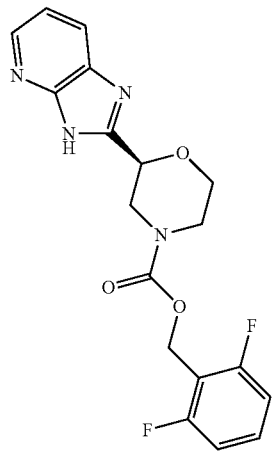 [SMILES: O=C(OCc1c(F)cccc1F)N1CCO[C@H](c2nc3cccnc3[nH]2)C1]

HPLC-MS Method: Z003_S05; R_t [min]: 0.98 MS: 375 (M+H)⁺ R_t [min]: 2.28

Chiral SFC Method: I C4_30_MeOH_NH₃_001

¹H NMR (400 MHz, DMSO-d₆); δ ppm: 3.10 (br s, 1H); 3.17-3.26 (m, 1H); 3.70 (br s, 1H); 3.85 (br s, 1H); 4.00 (br s, 1H); 4.21 (br s, 1H); 4.79 (br d, J=8.49 Hz, 1H); 5.17-5.25 (m, 2H); 7.10-7.23 (m, 3H); 7.46-7.55 (m, 1H); 7.92 (br d, J=6.72 Hz, 1H); 8.32 (br d, J=4.06 Hz, 1H); 12.99 (br s, 1H)

Example 17

Example 17 was prepared in analogy to Example 1. Starting materials: Example 3b (70 mg; 0.25 mmol), Phenyl-methanol (78 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 26 mg.

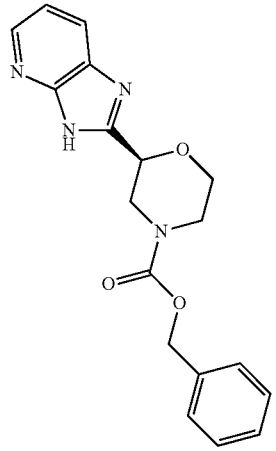 [SMILES: O=C(OCc1ccccc1)N1CCO[C@H](c2nc3cccnc3[nH]2)C1]

HPLC-MS Method: Z003_S05; R_t [min]: 0.97 MS: 339 (M+H)⁺ R_t [min]: 3.10

Chiral SFC Method: I C4_30_MeOH_NH₃_001

¹H NMR (400 MHz, DMSO-d₆); δ ppm: 3.03-3.24 (m, 1H); 3.72 (td, J=11.37, 2.60 Hz, 1H); 3.89 (br d, J=13.31 Hz, 1H); 4.02 (br d, J=11.28 Hz, 1H); 4.30 (br d, J=12.93 Hz, 1H); 4.82 (dd, J=10.14, 3.04 Hz, 1H); 5.10-5.19 (m, 2H); 7.22 (dd, J=7.98, 4.82 Hz, 1H); 7.31-7.42 (m, 5H); 7.93 (br d, J=7.73 Hz, 1H); 8.33 (dd, J=4.69, 1.27 Hz, 1H); 13.01 (br s, 1H)

Example 18

Example 18 was prepared in analogy to Example 1. Starting materials: Example 3b (70 mg; 0.25 mmol), p-Tolyl-methanol (92.6 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained 25 mg.

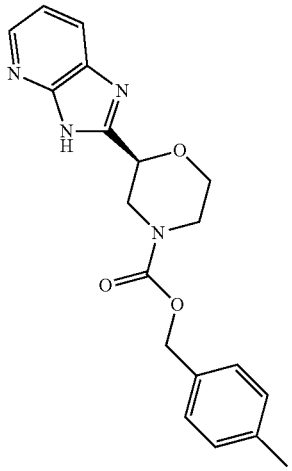 [SMILES: Cc1ccc(COC(=O)N2CCO[C@H](c3nc4cccnc4[nH]3)C2)cc1]

HPLC-MS Method: Z003_S05; $R_t$ [min]: 1.05 MS: 353 (M+H)$^+$ $R_t$ [min]: 3.61

Chiral SFC Method: I C4_30_EtOH_NH$_3$_001

$^1$H NMR (400 MHz, DMSO-d$_6$); δ ppm: 2.28-2.33 (m, 3H); 3.15 (br d, J=12.13 Hz, 2H); 3.65-3.77 (m, 1H); 3.87 (br d, J=13.14 Hz, 1H); 4.01 (br d, J=10.61 Hz, 1H); 4.28 (br d, J=13.39 Hz, 1H); 4.80 (dd, J=10.23, 2.91 Hz, 1H); 5.05-5.12 (m, 2H); 7.17-7.31 (m, 5H); 7.92 (br d, J=7.58 Hz, 1H); 8.32 (d, J=3.54 Hz, 1H)

Example 19

Example 19 was prepared in analogy to Example 1. Starting materials: Example 3b (70 mg; 0.25 mmol), (2,4-Difluoro-phenyl)-methanol (84.6 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained: 65 mg.

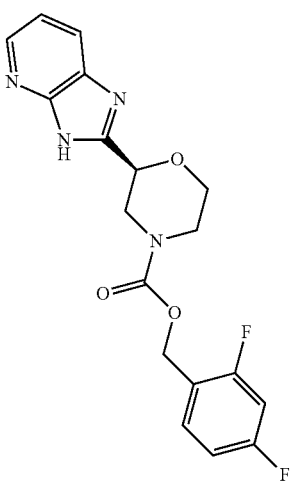 [SMILES: O=C(OCc1ccc(F)cc1F)N1CCO[C@H](c2nc3cccnc3[nH]2)C1]

HPLC-MS Method: Z003_S05; $R_t$ [min]: 1.01 MS: 375 (M+H)$^+$ $R_t$ [min]: 2.14

Chiral SFC Method: I C4_30_MeOH_NH$_3$_001

$^1$H NMR (400 MHz, DMSO-d$_6$); δ ppm: 3.02-3.22 (m, 1H); 3.71 (br t, J=10.48 Hz, 1H); 3.84 (br d, J=13.39 Hz, 1H); 4.00 (br d, J=11.37 Hz, 1H); 4.25 (br d, J=9.60 Hz, 1H); 4.81 (dd, J=10.11, 3.03 Hz, 1H); 5.11-5.21 (m, 2H); 7.11 (td, J=8.59, 2.02 Hz, 1H); 7.19-7.32 (m, 2H); 7.52-7.64 (m, 1H); 7.92 (br d, J=7.33 Hz, 1H); 8.33 (d, J=3.79 Hz, 1H) 12.97 (br s, 1H)

Example 24

Example 24 was prepared in analogy to Example 1. Starting materials: Example 3b (70 mg; 0.25 mmol), (3,4-Difluoro-phenyl)-methanol (86.53 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained: 56 mg

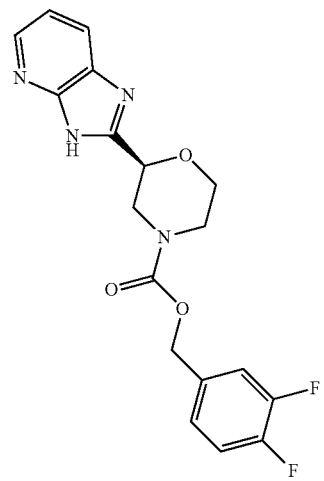 [SMILES: O=C(OCc1ccc(F)c(F)c1)N1CCO[C@H](c2nc3cccnc3[nH]2)C1]

HPLC-MS Method: Z003_S05; $R_t$ [min]: 1.01 MS: 375 (M+H)$^+$ $R_t$ [min]: 2.37

Chiral SFC Method: I C4_30_EtOH_NH$_3$_001

$^1$H NMR (400 MHz, DMSO-d$_6$); δ ppm: 3.05-3.25 (m, 1H); 3.73 (td, J=11.34, 2.66 Hz, 1H); 3.87 (br d, J=12.67 Hz, 1H); 4.01 (br d, J=11.66 Hz, 1H); 4.28 (br d, J=13.18 Hz, 1H); 4.83 (dd, J=10.01, 2.91 Hz, 1H); 5.07-5.17 (m, 2H); 7.19-7.31 (m, 2H); 7.40-7.54 (m, 2H); 7.93 (br d, J=7.48 Hz, 1H); 8.33 (dd, J=4.69, 1.27 Hz, 1H); 13.01 (br s, 1H)

Example 25

Example 25 was prepared in analogy to Example 1. Starting materials: Example 3b (70 mg; 0.25 mmol), (4-Chloro-3-fluoro-phenyl)-methanol (90.5 μl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 39 mg

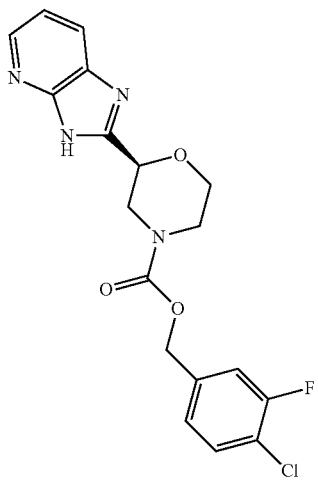 [SMILES: O=C(OCc1ccc(Cl)c(F)c1)N1CCO[C@H](c2nc3cccnc3[nH]2)C1]

HPLC-MS Method: Z003_S05; R$_t$ [min]: 1.06 MS: 391 (M+H)$^+$ R$_t$ [min]: 3.28

Chiral SFC Method: I C4_30_EtOH_NH$_3$_001

$^1$H NMR (400 MHz, DMSO-d$_6$); δ ppm; 3.05-3.25 (m, 1H); 3.42 (br s, 1H); 3.73 (td, J=11.25, 2.47 Hz, 1H); 3.88 (br s, 1H); 4.01 (br d, J=11.53 Hz, 1H); 4.28 (br d, J=13.43 Hz, 1H); 4.84 (br d, J=7.86 Hz, 1H); 5.10-5.20 (m, 2H); 7.19-7.32 (m, 2H); 7.47 (d, J=9.95 Hz, 1H); 7.60 (t, J=7.98 Hz, 1H); 7.93 (br d, J=7.35 Hz, 1H); 8.33 (d, J=3.80 Hz, 1H); 13.01 (br s, 1H)

Example 26

Example 26 was prepared in analogy to Example 1. Starting materials: Example 3b (70 mg; 0.25 mmol), [4-(difluoromethyl)phenyl]-methanol (79.9 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC. Obtained: 74 mg

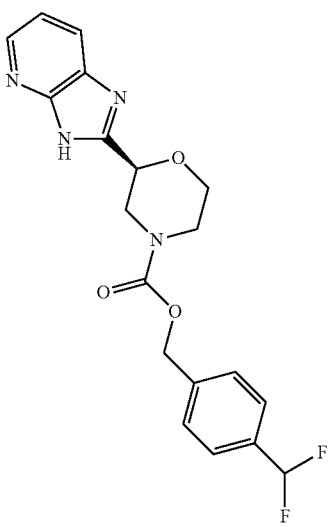 [SMILES: O=C(OCc1ccc(C(F)F)cc1)N1CCO[C@H](c2nc3cccnc3[nH]2)C1]

HPLC-MS Method: Z003_S05; R$_t$ [min]: 0.99 MS: 389 (M+H)$^+$ R$_t$ [min]: 2.66

Chiral SFC Method: I C4_30_EtOH_NH$_3$_001

$^1$H NMR (400 MHz, DMSO-d$_6$); δ ppm: 3.04-3.24 (m, 1H); 3.63-3.85 (m, 1H); 3.85-3.94 (m, 1H); 4.02 (br d, J=11.41 Hz, 1H); 4.26-4.34 (m, 1H); 4.84 (dd, J=10.01, 2.66 Hz, 1H); 5.16-5.25 (m, 2H); 7.03 (s, 1H); 7.16-7.24 (m, 1H); 7.33-7.60 (m, 4H); 7.93 (br d, J=7.73 Hz, 1H); 8.33 (dd, J=4.69, 1.39 Hz, 1H); 13.01 (br s, 1H)

Example 27

Example 27 was prepared in analogy to Example 1. Starting materials: Example 3b (70 mg; 0.25 mmol), (2-Fluoro-phenyl)-methanol (81.5 µl; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained: 40 mg

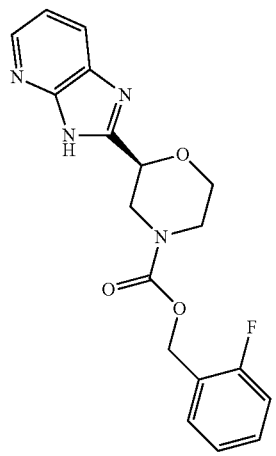 [SMILES: O=C(OCc1ccccc1F)N1CCO[C@H](c2nc3cccnc3[nH]2)C1]

HPLC-MS Method: Z003_S05; R$_t$ [min]: 0.99 MS: 357 (M+H)$^+$ R$_t$ [min]: 2.66

Chiral SFC Method: I C4_30_MeOH_NH$_3$_001

$^1$H NMR (400 MHz, DMSO-d$_6$); δ ppm: 3.01-3.21 (m, 1H); 3.72 (br t, J=10.39 Hz, 1H); 3.86 (br d, J=13.31 Hz, 1H); 4.01 (br d, J=10.52 Hz, 1H); 4.27 (br d, J=12.29 Hz, 1H); 4.82 (dd, J=10.14, 2.91 Hz, 1H); 5.16-5.24 (m, 2H); 7.19-7.27 (m, 1H); 7.39-7.53 (m, 2H); 7.93 (br d, J=7.35 Hz, 1H); 8.33 (d, J=4.70 Hz, 1H); 13.01 (br s, 1H)

Example 28

Example 28 was prepared in analogy to Example 1. Starting materials: Example 3b (70 mg; 0.25 mmol), (4-Chloro-phenyl)-methanol (108 mg; 0.76 mmol); 1-1'-CDI (123 mg; 0.76 mmol); DIPEA (0.13 ml; 0.76 mmol). Solvent: DMF (3 ml).

The crude obtained after work up was purified by semi-preparative HPLC.

Obtained: 44 mg

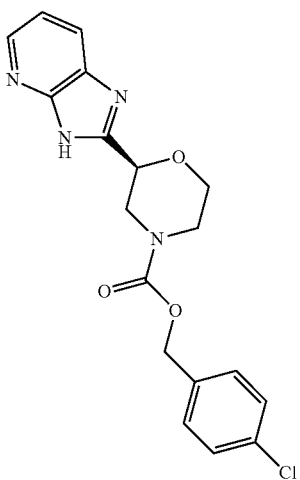 [SMILES: O=C(OCc1ccc(Cl)cc1)N1CCO[C@H](c2nc3cccnc3[nH]2)C1]

HPLC-MS Method: Z003_S05; R$_t$ [min]: 1.05 MS: 373 (M+H)$^+$ R$_t$ [min]: 3.52

Chiral SFC Method: I C4_30_MeOH_NH$_3$_001

$^1$H NMR (400 MHz, DMSO-d$_6$); δ ppm: 3.05-3.22 (m, 1H); 3.72 (td, J=11.34, 2.66 Hz, 1H); 3.87 (br d, J=13.31 Hz, 1H); 4.01 (br d, J=11.28 Hz, 1H); 4.28 (br d, J=13.05 Hz, 1H); 4.83 (dd, J=10.01, 2.91 Hz, 1H); 5.13 (d, J=2.79 Hz, 2H); 7.22 (dd, J=7.98, 4.69 Hz, 1H); 7.44 (s, 4H); 7.93 (br d, J=7.73 Hz, 1H); 8.33 (dd, J=4.69, 1.27 Hz, 1H); 13.01 (br s, 1H)

Example 30

A mixture of example 3d (200 mg, 0.68 mmol), example 4b (180 mg, 0.68 mmol) and TEA (300 μL, 2.2 mmol) in ACN (5 mL) was stirred at ambient temperature for 0.5 h. After addition of aqueous ammonia (conc.) and evaporation, the residue was purified by preparative HPLC (C-18 X-Bridge; 50° C.; H$_2$O+0.15% ammonia:acetonitrile=80:20>60:40) to obtain 225 mg of the desired product.

HPLC-MS; Method: Z018_S04; R$_t$ [min]: 0.97 MS: 371 (M+H)$^+$ $^1$H NMR (400 MHz, DMSO-d$_6$); δ ppm: 2.27-2.33 (m, 4H); 3.02-3.22 (m, 1H); 3.66-3.76 (m, 1H); 3.86 (br d, J=13.89 Hz, 1H); 4.01 (br d, J=10.86 Hz, 1H); 4.27 (br d, J=13.39 Hz, 1H); 4.81 (dd, J=10.11, 3.03 Hz, 1H); 5.05-5.12 (m, 2H); 7.15-7.30 (m, 5H); 7.86 (br d, J=8.34 Hz, 1H); 8.33 (t, J=2.15 Hz, 1H); 13.18 (br s, 1H)

A sample of the product of example 30 (225 mg) was separated by chiral chromatography (SFC) to get access to Ex. 31.

Preparative Conditions:

| Column | CHIRAL ART ® Amylose-SA_20 × 250 mm_5 μm |
|---|---|
| Solvents: | |
| scCO2 | 75% |
| MeOH 20 mM NH$_3$ | 25% |
| Backpressure regulator | 150 bar |
| Temperature | 40° C. |
| Flowrate | 60 ml/min |
| Sample concentration | 14 mg/ml |
| Sample solvent | MeOH:DCM 2:1 |
| Injection Volume | 300 μl |
| Detector wavelength | 220 nm |
| Device | Sepiatec 1 Prep SFC 100 |

Example 31

Obtained: 103 mg

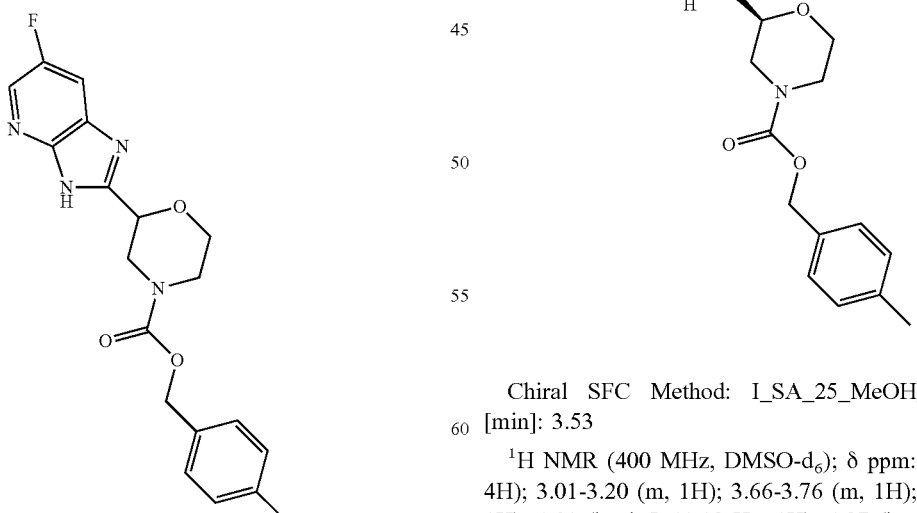

Chiral SFC Method: I_SA_25_MeOH_NH$_3$_001 R$_t$ [min]: 3.53

$^1$H NMR (400 MHz, DMSO-d$_6$); δ ppm: 2.28-2.33 (m, 4H); 3.01-3.20 (m, 1H); 3.66-3.76 (m, 1H); 3.81-3.96 (m, 1H); 4.01 (br d, J=11.12 Hz, 1H); 4.27 (br d, J=13.14 Hz, 1H); 4.80 (dd, J=10.11, 3.03 Hz, 1H); 5.04-5.13 (m, 2H); 7.18 (d, J=8.08 Hz, 2H); 7.29 (d, J=7.83 Hz, 2H); 7.86 (br d, J=7.33 Hz, 1H); 8.33 (t, J=2.15 Hz, 1H)

The invention claimed is:
1. A compound of formula A

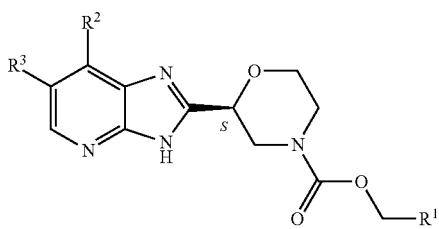

or a pharmaceutically acceptable salt thereof,
in which
R¹ represents phenyl which is optionally substituted with 1 to 3 substituents selected from the group consisting of fluoro, chloro, methyl, ethyl, cyclopropyl, $F_2HC$, $FH_2C$, $F_3C$—;
R² represents hydrogen, methyl; and
R³ represents hydrogen, fluoro.

2. The compound according to claim 1, or a pharmaceutically acceptable salt thereof, wherein
R² represents hydrogen; and
R³ represents hydrogen.

3. The compound according to claim 1, or a pharmaceutically acceptable salt thereof, wherein
R¹ represents phenyl which is optionally substituted with 1 or 2 substituents selected from the group consisting of fluoro, chloro, methyl, and $F_2HC$—.

4. The compound according to claim 2, or a pharmaceutically acceptable salt thereof, wherein
R¹ represents phenyl which is optionally substituted with 1 or 2 substituents selected from the group consisting of fluoro, chloro, methyl, and $F_2HC$—.

5. The compound according to claim 1, or a pharmaceutically acceptable salt thereof, wherein
R¹ represents

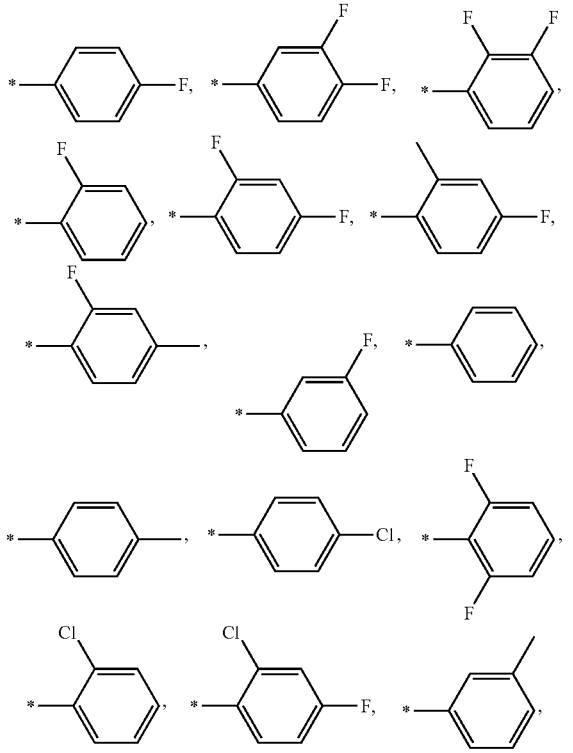

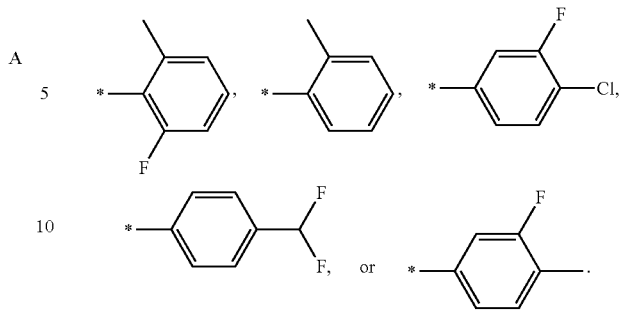

wherein * represents a bonding position of R¹ to the compound of formula A.

6. The compound according to claim 2, or a pharmaceutically acceptable salt thereof, wherein
R¹ represents

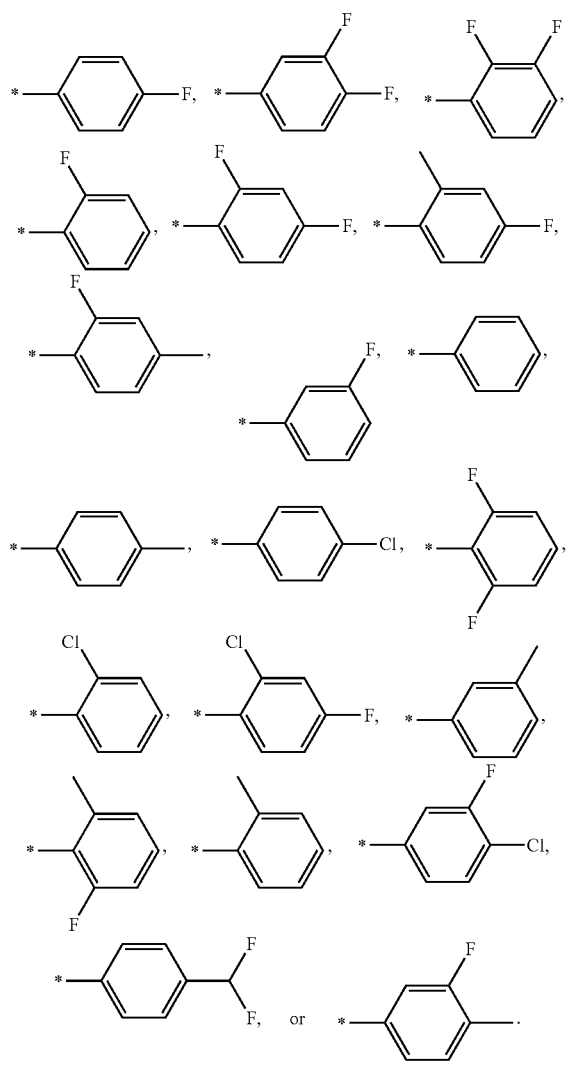

7. The (S)-enantiomer according to claim 1, or a pharmaceutically acceptable salt thereof, selected from the group consisting of

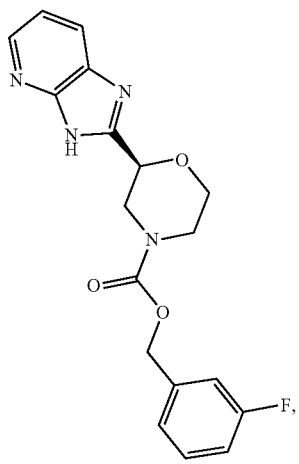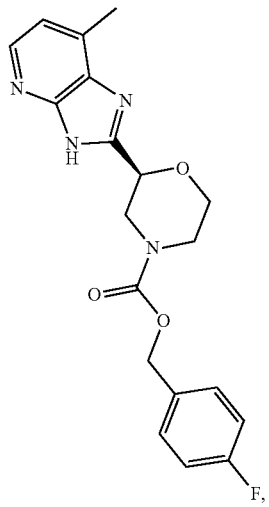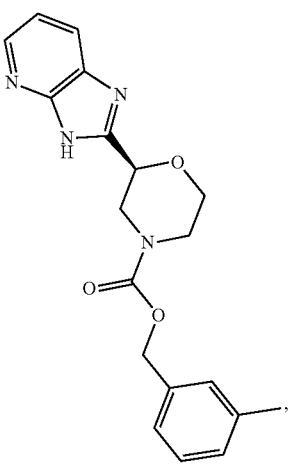

10
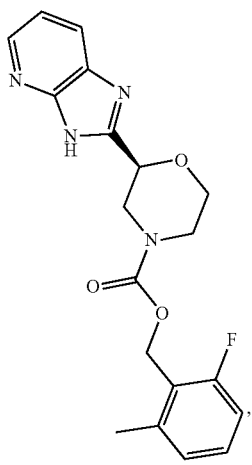
11
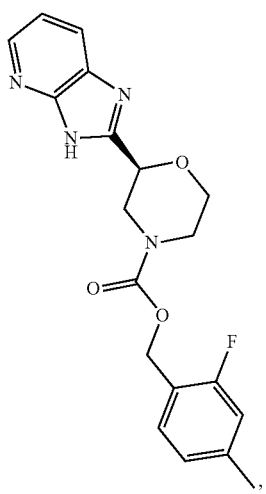
12
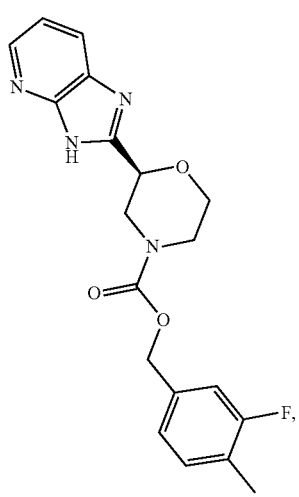
13
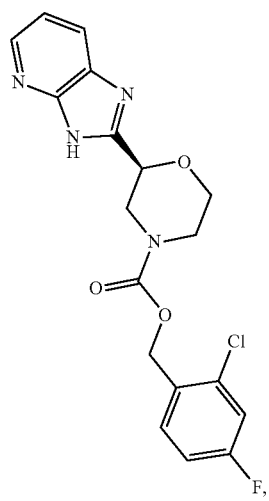
14
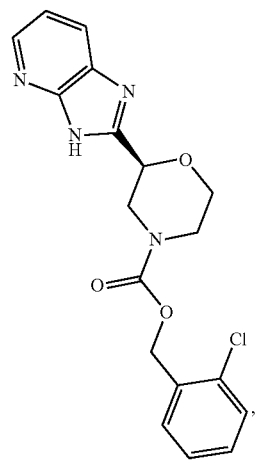
15
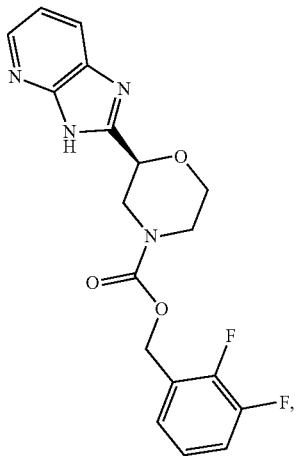

16
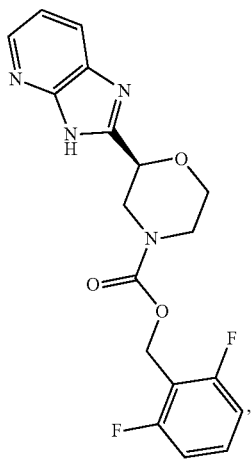
17
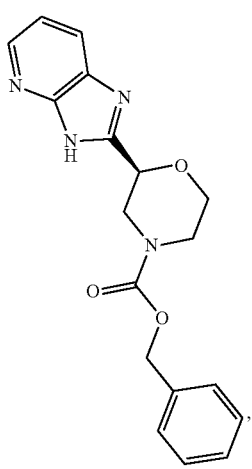
18
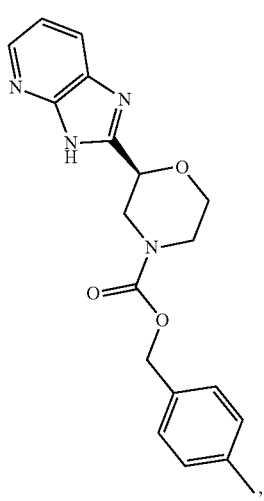
19
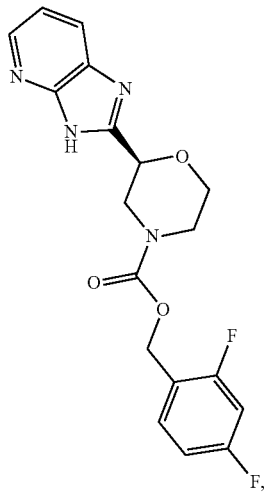
24
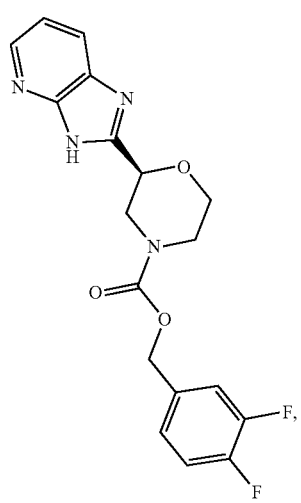
25
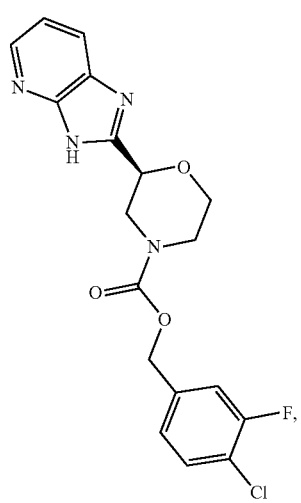

-continued

26

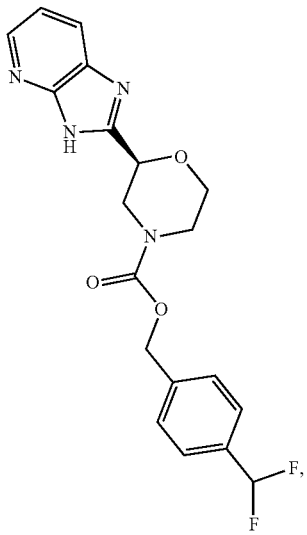

27

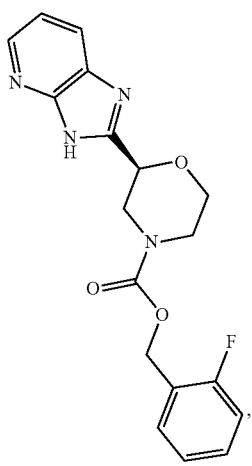

28

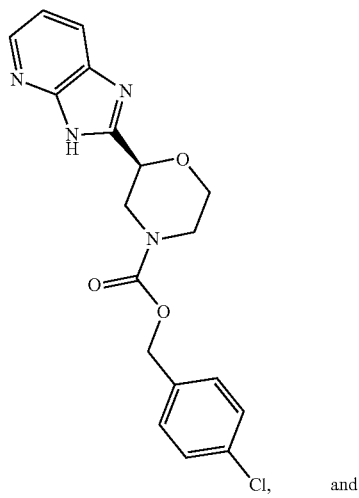
Cl, and

-continued

5

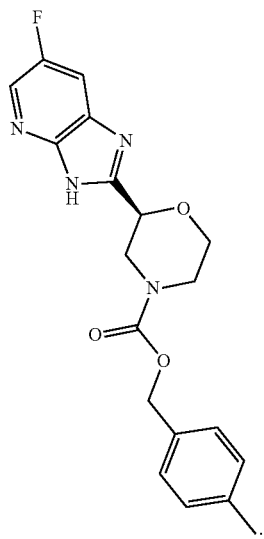

8. A pharmaceutically acceptable salt of the compound according to claim 1.

9. A method for treating or preventing a psychiatric disorder or disease, comprising administering the compound of formula A according to claim 1, or a pharmaceutically acceptable salt thereof, to a patient in need thereof of wherein the psychiatric disorder or disease is bipolar disorder I depressed, hypomanic, manic and mixed form; bipolar disorder II; single depressive episode, recurrent major depressive disorder, minor depressive disorder, depressive disorder with postpartum onset, depressive disorders with psychotic symptoms; major depressive disorder with or without concomitant anxious distress, mixed features, melancholic features, atypical features, mood-congruent psychotic features, mood-incongruent psychotic features, or catatonia.

10. The method according to claim 9, further comprising administering the compound of formula A, or a pharmaceutically acceptable salt thereof, in combination with another antidepressant drug.

11. The method according to claim 9, wherein the patient is further undergoing behavioral therapy.

12. A pharmaceutical composition comprising the compound according to claim 1, or a pharmaceutically acceptable salt thereof, in admixture with a pharmaceutically acceptable adjuvant, diluent and/or carrier.

13. The compound according to claim 1 having the structure:

2

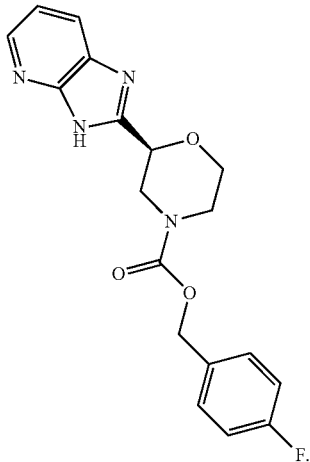

14. The compound according to claim 1 having the structure:

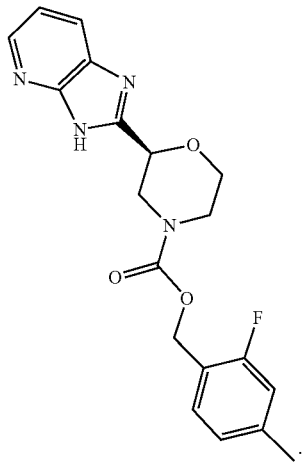

11

15. The compound according to claim 1 having the structure:

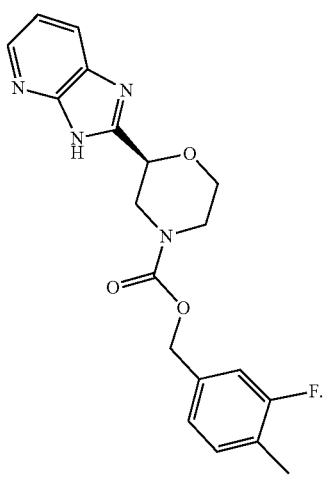

12

16. The compound according to claim 1 having the structure:

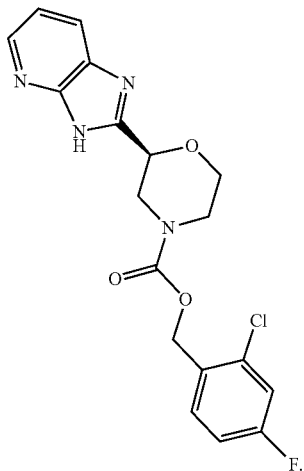

13

17. The compound according to claim 1 having the structure:

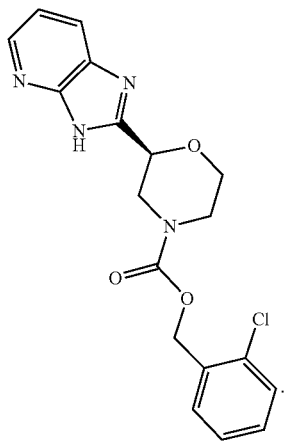

14

18. The compound according to claim 1 having the structure:

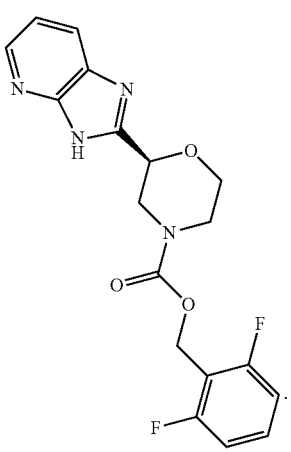

16

19. The compound according to claim 1 having the structure:

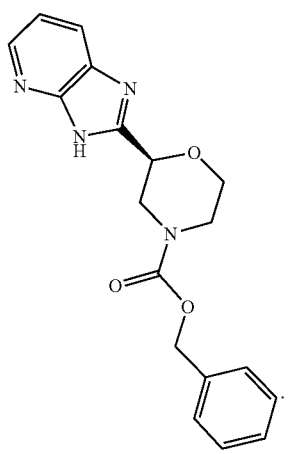

17

20. The compound according to claim 1 having the structure:

21. The compound according to claim 1 having the structure:
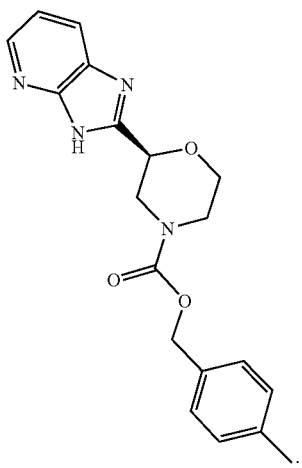
22. The compound according to claim 1 having the structure:
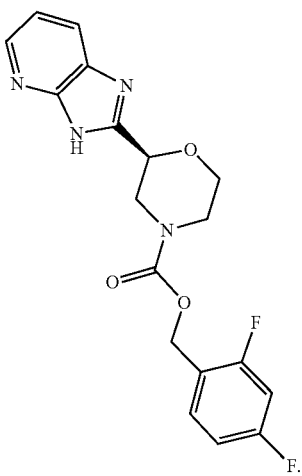
23. The compound according to claim 1 having the structure:
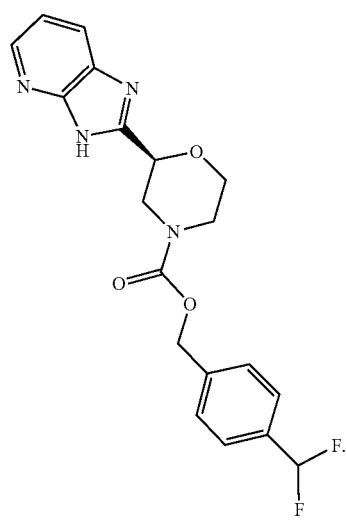
24. The compound according to claim 1 having the structure:
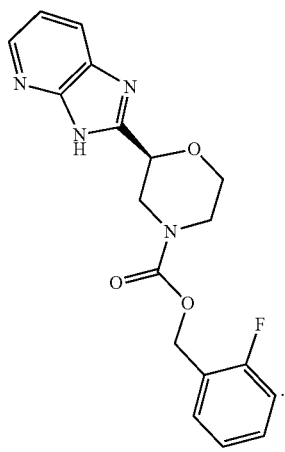
25. The compound according to claim 1 having the structure:
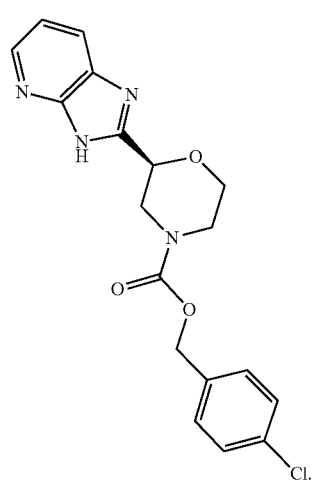
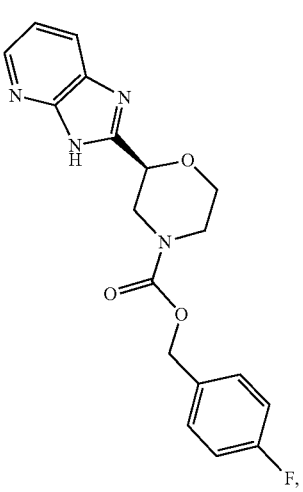
or a pharmaceutically acceptable salt thereof.

26. The compound according to claim 1 having the structure:

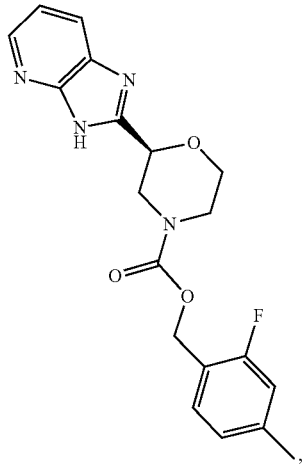

11 or a pharmaceutically acceptable salt thereof.

27. The compound according to claim 1 having the structure:

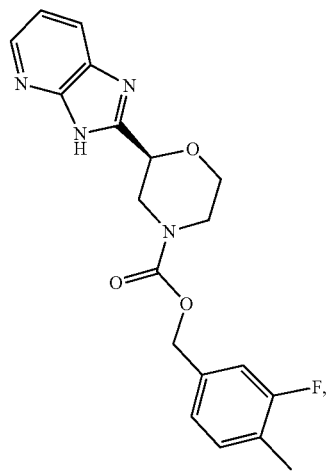

12 or a pharmaceutically acceptable salt thereof.

28. The compound according to claim 1 having the structure:

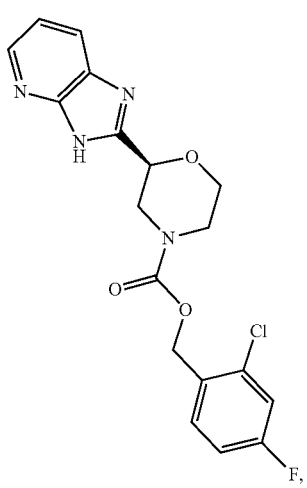

13 or a pharmaceutically acceptable salt thereof.

29. The compound according to claim 1 having the structure:

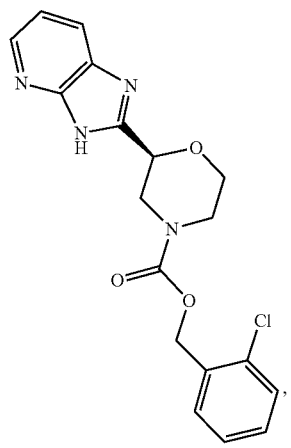

14 or a pharmaceutically acceptable salt thereof.

30. The compound according to claim 1 having the structure:

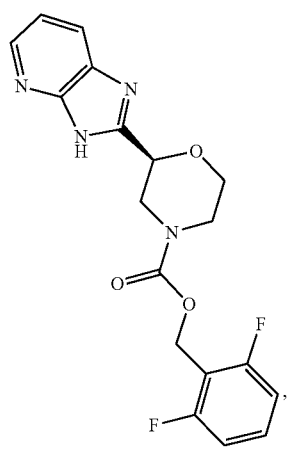

16 or a pharmaceutically acceptable salt thereof.

31. The compound according to claim 1 having the structure:

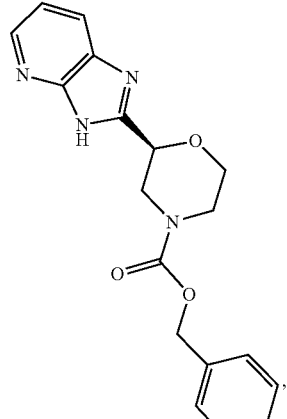

17 or a pharmaceutically acceptable salt thereof.

32. The compound according to claim 1 having the structure:

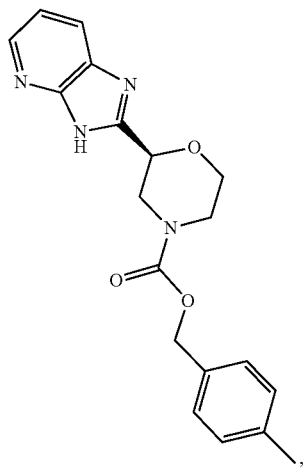 [SMILES: Cc1ccc(COC(=O)N2CCO[C@H](c3nc4cccnc4[nH]3)C2)cc1]

or a pharmaceutically acceptable salt thereof.

33. The compound according to claim 1 having the structure:

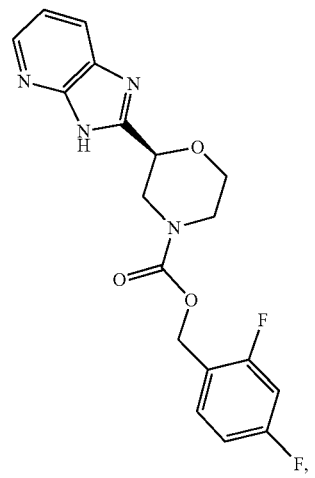

or a pharmaceutically acceptable salt thereof.

34. The compound according to claim 1 having the structure:

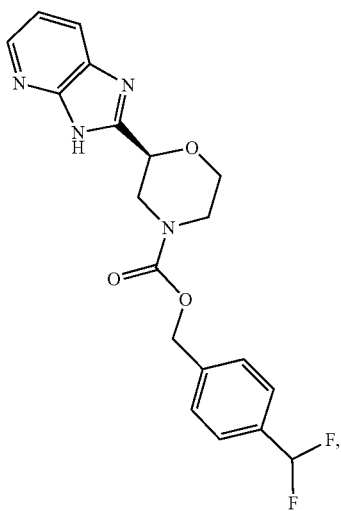

or a pharmaceutically acceptable salt thereof.

35. The compound according to claim 1 having the structure:

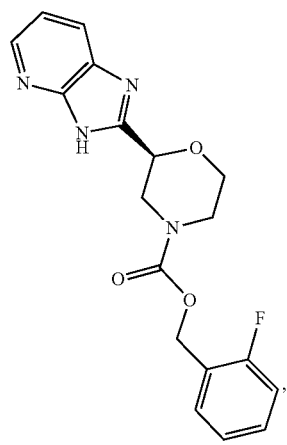

or a pharmaceutically acceptable salt thereof.

36. The compound according to claim 1 having the structure:

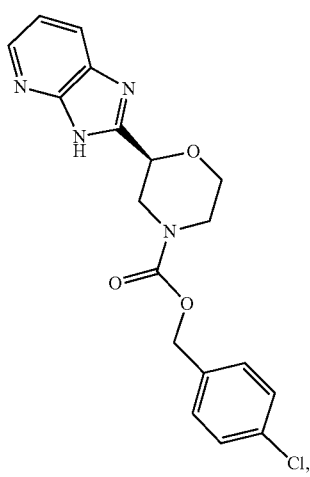

or a pharmaceutically acceptable salt thereof.

37. The (S)-enantiomer according to claim 1, selected from the group consisting of

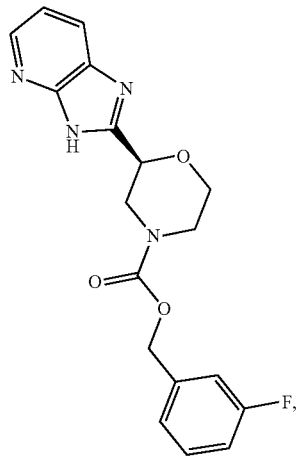

2
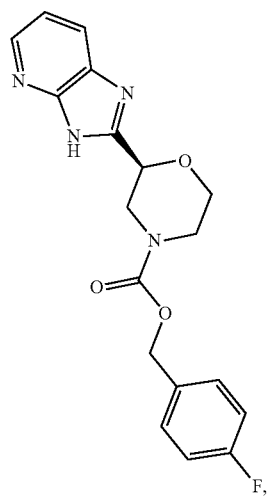
4
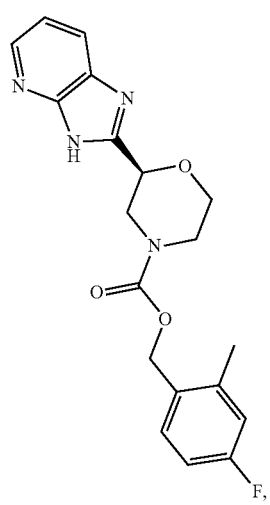
6
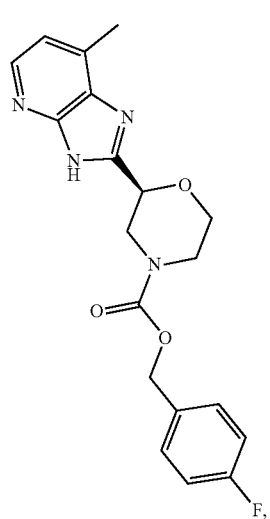
8
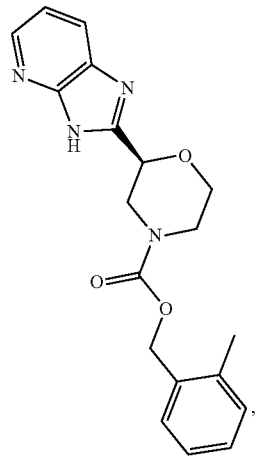
9
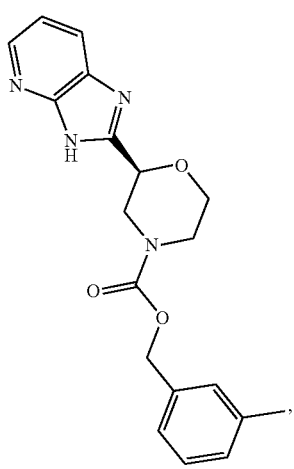
10
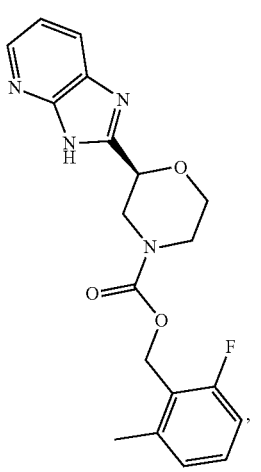

11
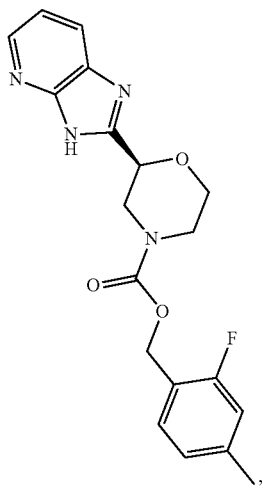
12
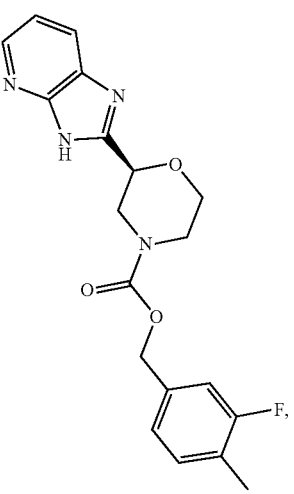
13
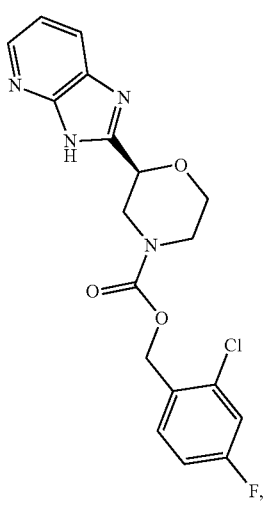
14
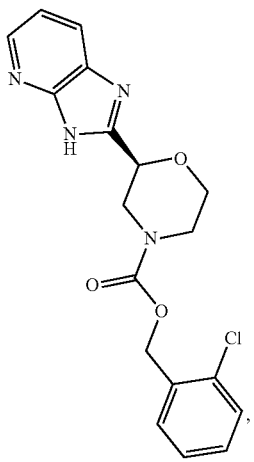
15
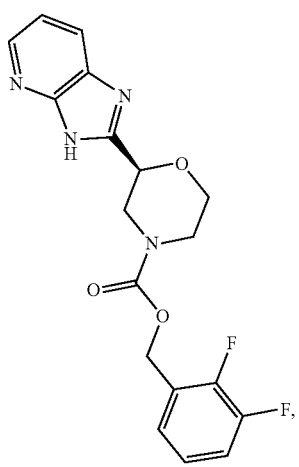
16
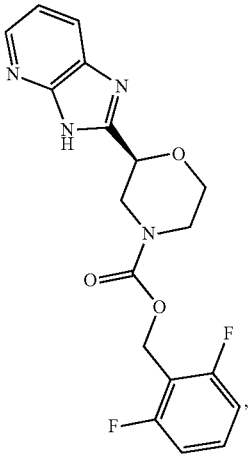

17
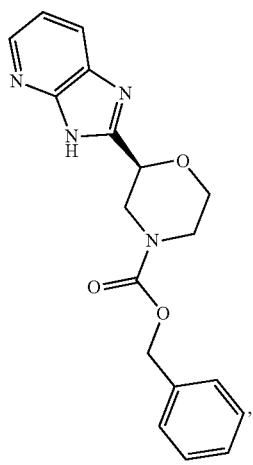
18
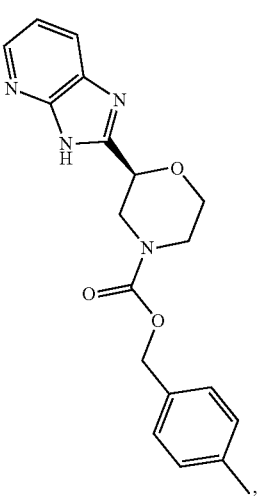
19
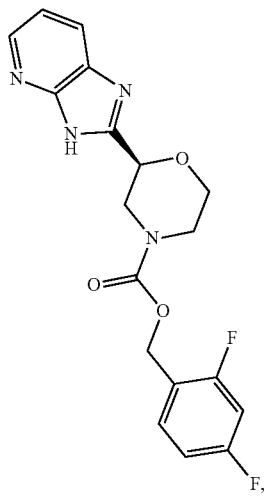
24
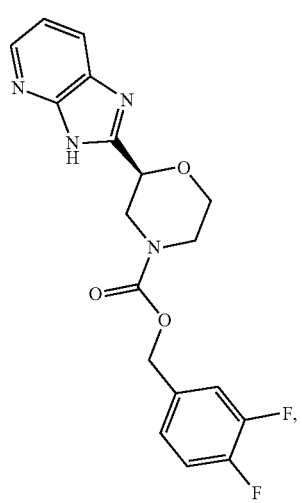

25
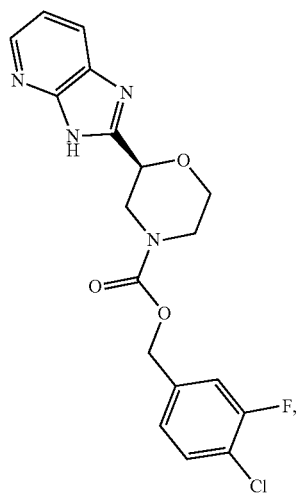
26
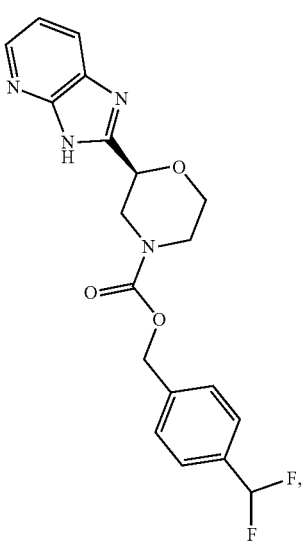
27
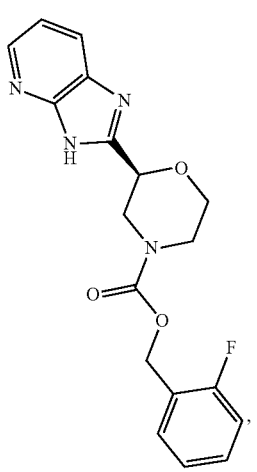
28
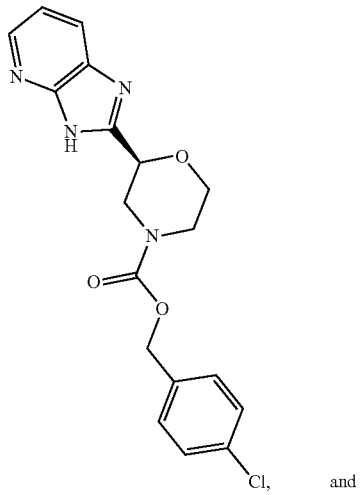
and
31
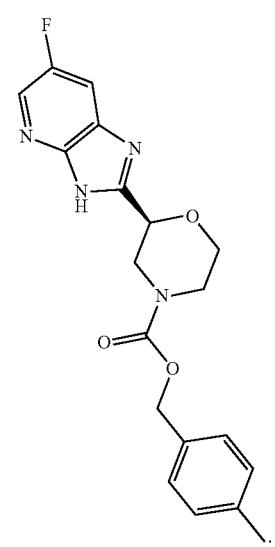
38. A (S)-enantiomer of a compound having the structure:
2
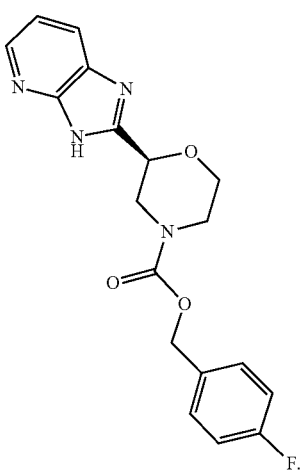

39. A (S)-enantiomer of a compound having the structure:
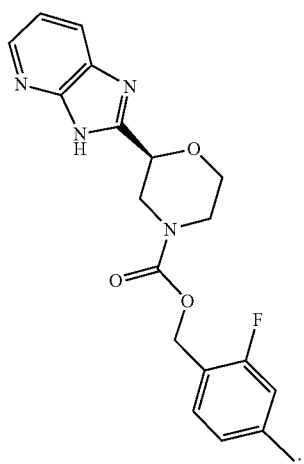
40. A (S)-enantiomer of a compound having the structure:
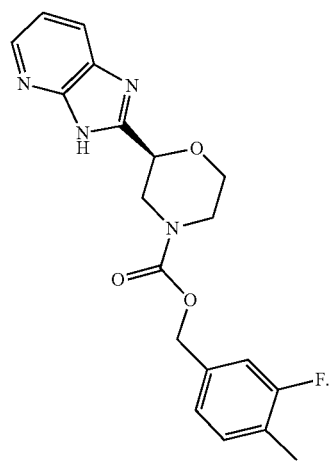
41. A (S)-enantiomer of a compound having the structure:
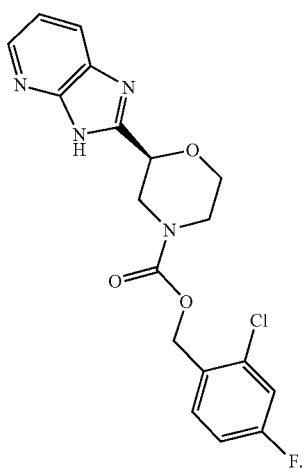
42. A (S)-enantiomer of a compound having the structure:
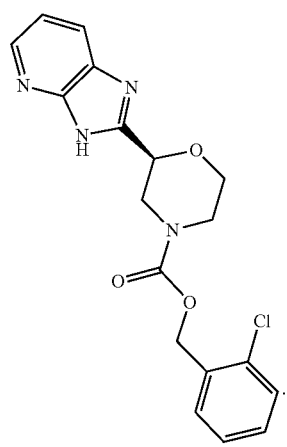
43. A (S)-enantiomer of a compound having the structure:
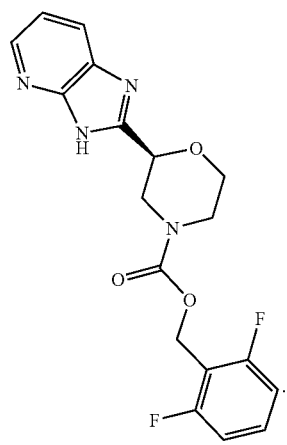
44. A (S)-enantiomer of a compound having the structure:
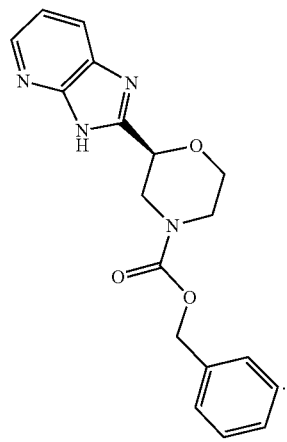

45. A (S)-enantiomer of a compound having the structure:
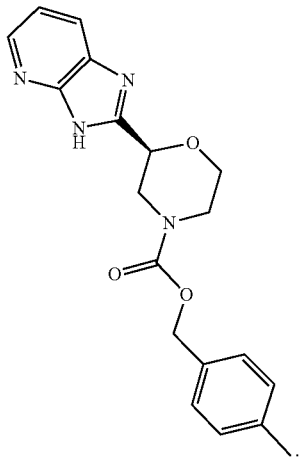
18
46. A (S)-enantiomer of a compound having the structure:
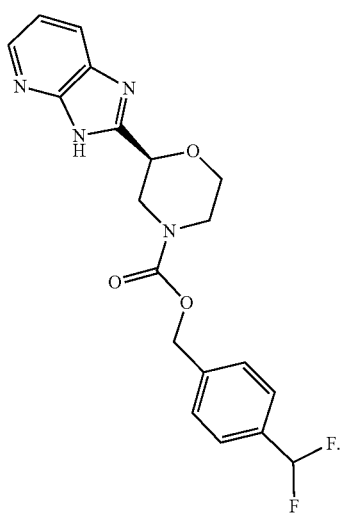
19
47. A (S)-enantiomer of a compound having the structure:
26
48. A (S)-enantiomer of a compound having the structure:
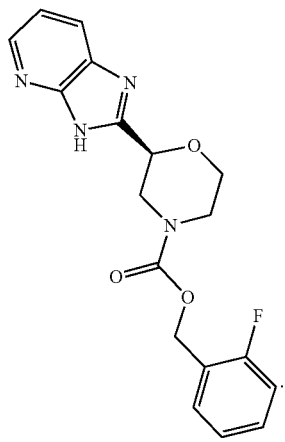
27
49. A (S)-enantiomer of a compound having the structure:
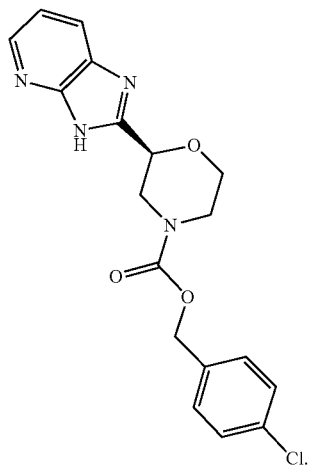
28
\* \* \* \* \*